US007745175B2

(12) United States Patent
Ainley et al.

(10) Patent No.: US 7,745,175 B2
(45) Date of Patent: Jun. 29, 2010

(54) **POLYNUCLEOTIDES ENCODING *CLOSTRIDIUM PERFRINGENS* ALPHA TOXIN PROTEINS**

(75) Inventors: William M. Ainley, Carmel, IN (US); Janna Armstrong, Indianapolis, IN (US); Krishna Madduri, Westfield, IN (US); Donald J. Merlo, Carmel, IN (US); Kelley A. Smith, Lebanon, IN (US); Mark A. Thompson, Zionsville, IN (US); Steven R. Webb, Westfield, IN (US); Liu Y. Shen, Westfield, IN (US)

(73) Assignee: Dow AgroSciences LLC, Indianpolis, IN (US)

( * ) Notice: Subject to any disclaimer, the term of this patent is extended or adjusted under 35 U.S.C. 154(b) by 0 days.

(21) Appl. No.: 11/925,300

(22) Filed: Oct. 26, 2007

(65) Prior Publication Data

US 2008/0102079 A1  May 1, 2008

Related U.S. Application Data

(60) Provisional application No. 60/854,741, filed on Oct. 27, 2006.

(51) Int. Cl.
*A61K 8/00* (2006.01)
*C07H 21/04* (2006.01)
(52) U.S. Cl. ............... 435/69.3; 435/71.1; 435/71.2; 435/71.3; 536/23.7
(58) Field of Classification Search ................ None
See application file for complete search history.

(56) References Cited

U.S. PATENT DOCUMENTS 6,248,329 B1 * 6/2001 Chandrashekar et al. . 424/191.1

FOREIGN PATENT DOCUMENTS

WO WO 2006/113772 A 10/2006

OTHER PUBLICATIONS

The Dictionary of Immunology, Herbert et al eds, Academic Press, one page 1995.*
Feng et al (Infection and Immunity, 64(1):363-365, 1996).*
Ellis, R.W. (Chapter 29 of "Vaccines" [Plotkin, S.A. et al. (eds) published by W. B. Saunders company (Philadelphia) in 1988, especially p. 571.*
Sheedy et al (Journal of Clinical Microbiology, 42(3):1345-1347, 2004).*
Database EMBL, "*Clostridium perfringens* strain NRRL B-23700 phospholipasae C (plc) gene, complete cds." Accession No. DQ184119, May 5, 2006.
Database UniProt, "*Phospholipasae C*." Accession No. Q1HXE9, Jun. 13, 2006.
Guillouard, I., et al. "Use of site-directed mutagenesis to probe structure-function relationships of alpha-toxin from *Clostridium perfringens.*" *Infection and Immunity*, Jul. 1996, pp. 2440-2444, vol. 64, No. 7.
Nagahama, M., et al. "Site-directed mutagenesis of histidine residues in *Clostridium perfringes* alpha-toxin" *Journal of Bacteriology*, Mar. 1995, pp. 1179-1185, vol. 177, No. 5.
Nagahama, M., et al. "Site-specific mutagenesis of *Clostridium perfringens* alpha-toxin: replacement of Asp-56, Asp-130, or Glu-152 causes loss of enzymatic and hemolytic activities." *Infection and Immunity*, Aug. 1997, pp. 3489-3492, vol. 65, No. 8.
Rooney, A., et al. "Analysis of core housekeeping and virulence genes reveals cryptic lineages of *Clostridium perfringens* that are associated with distinct disease presentations." *Genetics*, Apr. 2006, pp. 2081-2092, vol. 172, No. 4.
Schoepe, H., et al. "Immunization with an alphatoxin variant 121A/91-R212H protects mice against *Clostridium perfringens* alphatoxin" *Anaerobe*, Feb. 2006, pp. 44-48, vol. 12, No. 1.
Schoepe, H., et al. "Naturally occurring *Clostridium perfringens* nontoxic alpha-toxin variant as a potential vaccine candidate against alpha-toxin-associated disease" *Infection and Immunity*, Nov. 2001, pp. 7194-7196, vol. 69, No. 11.
Williamson, E.D., et al. "A genetically engineered vaccine against the alpha-toxin of *Clostridium perfringens* protects mice against experimental gas gangrene." *Vaccine*, Sep. 1993, pp. 1253-1258, vol. 11, No. 12.

* cited by examiner

*Primary Examiner*—Patricia A Duffy
(74) *Attorney, Agent, or Firm*—Ronald S. Maciak; Baker & Daniels LLP

(57) ABSTRACT

This invention pertains in part to the development of a vaccine for poultry against necrotic enteritis (NE). The vaccine utilizes a protective antigen that is a mutated, full-length, non-toxic *Clostridium perfringens* (Cp) α-toxin protein (Mcpa). Utility of this vaccine was demonstrated by reduction of lesion severity in NE challenge trails, for example. Also disclosed herein are novel approaches for producing this vaccine in significant quantities. One exemplified approach involves producing NE vaccine (mutated alpha toxin) in bacterial expression systems, preferably utilizing the *Pseudomonas fluorescens* system, for commercial use in controlling NE in the poultry industry. The subject vaccines can be administered preferably to chickens in several different ways. A novel, Type VI alpha toxin from chicken isolates of Cp is also disclosed.

7 Claims, 12 Drawing Sheets

FIG. 1A

```
                       181                                                            240
     Swan PLC    (181) TFAEERKEQYKINTAGKTNEAFY TLNKDFNAWSKEYARSFAKTK YYSHAAMS
   Human CLOPLC  (181) TFAEERKEQYKINTAGKTNEAFY DILKNKDFNAWSKEYARGFAKTGKSIYYSHASMSH
   Bovine CLOCPA (181) TFAFFRKEQYKINTAGCKTNEDFYADILKNKDFNAWSKEYARGFAKTGKSIYYSHASMSH
 chicken type I PLC (181) TFAEERKEQYKINTAGCKTNEDFYADILKNKDFNAWSKEYARGFAKTGKSIYYSHASMSH
 chicken type II PLC (181) TFAEERKEQYKINTAGCKTNEDFYADILKNKDFNAWSKEYARGFAKTGKSIYYSHASMSH
 chicken type III PLC (181) TFAEERKEQYKINTAGCKTNEDFYADILKNKDFNAWSKEYARGFAKTGKSIYYSHASMSH
 chicken type IV PLC (181) TFAEERKEQYKINTAGCKTNEAFYTDILKNKDFNAWSKEYARGFAKTGKSIYYSHASMSH
 chicken type V PLC (181) TFAEERKEQYKINTAGCKTNEAFYADILKNKDFNAWSKEYARGFAKTGKSIYYSHASMSH
BBL Chicken alpha toxin (181) TFAEERKEQYKINTAGCKTNE FYADILKNKDFNAWSKEYARGFAKTGKSIYYSHASMSH
   Chicken PLC mutv1 (181)

241                                                            300
     Swan PLC    (241) SWDD WDYAAKV LANSQKGT GYIYRFLHDVSE   S KNV ELVAYI N GEK AGT
   Human CLOPLC  (241) SWDDWDYAAKVTLANSQKGTAGYIYRFLHDVSEGNDPSVGKNVKELVAYISTSGEKDAGT
   Bovine CLOCPA (241) SWDDWDYAAKVTLANSQKGTAGYIYRFLHDVSEGNDPSVGKNVKELVAYISTSGEKDAGT
 chicken type I PLC (241) SWDDWDYAAKVTLANSQKGTAGYIYRFLHDVSEGNDPSVGKNVKELVAYISTSGEKDAGT
 chicken type II PLC (241) SWDDWDYAAKVTLANSQKGTAGYIYRFLHDVSEGNDPSVGKNVKELVAYISTSGEKDAGT
 chicken type III PLC (241) SWDDWDYAAKVTLANSQKGTAGYIYRFLHDVSEGNDPSVGKNVKELVAYISTSGEKDAGT
 chicken type IV PLC (241) SWDDWDYAAKVTLANSQKGTAGYIYRFLHDVSEGNDPSVGKNVKELVAYISTSGEKDAGT
 chicken type V PLC (241) SWDDWDYAAKVTLANSQKGTAGYIYRFLHDVSEGNDPSVGKNVKELVAYISTSGEKDAGT
BBL Chicken alpha toxin (241) SWDDWDYAAKVTLANSQKGTAGYIYRFLHDVSEGNDPSVGKNVKELVAYISTSGEKDAGT
   Chicken PLC mutv1 (241)

301                                                            360
     Swan PLC    (301) DDYMYEGIKTKDG  TQEW MDNPGNDFMTGS DTYTFKLKD NLKIDDIQNMWIRK KYT
   Human CLOPLC  (301) DDYMYFGIKTKDGKTQEWEMDNPGNDFMTGSKDTYTFKLKDENLKIDDIQNMWIRKHKYT
   Bovine CLOCPA (301) DDYMYFGIKTKDGKTQEWEMDNPGNDFMTGSKDTYTFKLKDENLKIDDIQNMWIRKRKYT
 chicken type I PLC (301) DDYMYFGIKTKDGKTQEWEMDNPGNDFMTGSKDTYTFKLKDENLKIDDIQNMWIRKRKYT
 chicken type II PLC (301) DDYMYFGIKTKDGKTQEWEMDNPGNDFMTGSKDTYTFKLKDENLKIDDIQNMWIRKRKYT
 chicken type III PLC (301) DDYMYFGIKTKDGKTQEWEMDNPGNDFMTGSKDTYTFKLKDENLKIDDIQNMWIRKRKYT
 chicken type IV PLC (301) DDYMYFGIKTKDGKTQEWEMDNPGNDFMTGSKDTYTFKLKDENLKIDDIQNMWIRKRKYT
 chicken type V PLC (301) DDYMYFGIKTKDGKTQEWEMDNPGNDFMTGSKDTYTFKLKDENLKIDDIQNMWIRKRKYT
BBL Chicken alpha toxin (301) DDYMYFGIKTKDGKTQEWEMDNPGNDFMTGSKDTYTFKLKDENLKIDDIQNMWIRKRKYT
   Chicken PLC mutv1 (301) DDYMYFGIKTKDGKTQEWEMDNPGNDFMTGSKDTYTFKLKDENLKIDDIQNMWIRKRKYT
```

FIG. 1B

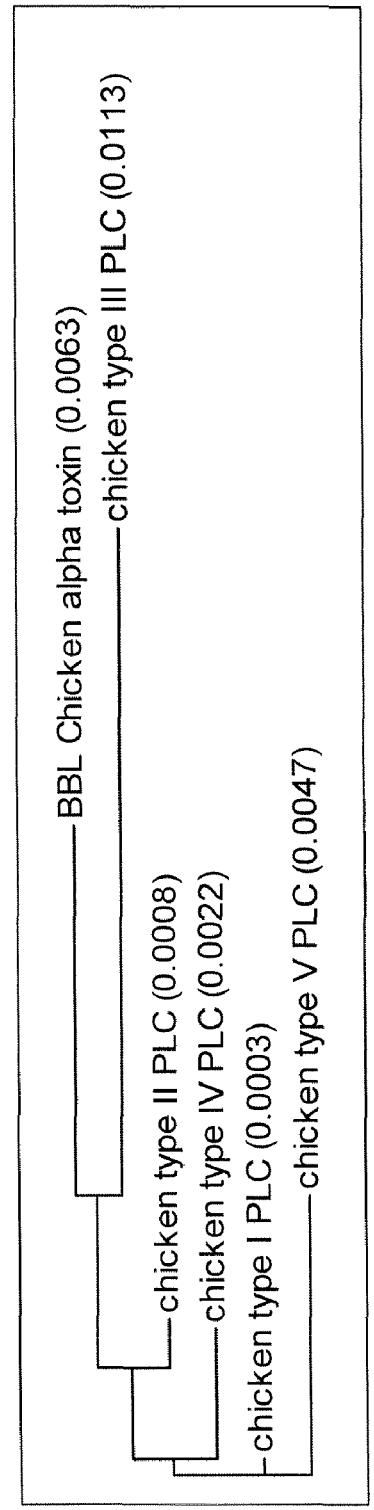

POLYNUCLEOTIDES ENCODING *CLOSTRIDIUM PERFRINGENS* ALPHA TOXIN PROTEINS

BACKGROUND OF THE INVENTION

*Clostridium perfringens* ("Cp"), a gram-positive anaerobe, is associated with a number of diseases including gas gangrene, sudden infant death syndrome, and necrotic enteritis in chickens (Titball et al., 1999). Necrotic enteritis (NE) is a serious, fatal, and prevalent disease in the poultry industry (Justin et al., 2002) that is characterized by acute enterotoxemia, resulting in small intestine necrosis and up to 50% mortality, primarily in chickens and turkeys from 2-12 weeks of age.

Preventive treatment with antibiotics is the predominant method currently employed to prevent Cp infections in the poultry industry. Due to widespread concern over development of antibiotic resistant bacterial strains, there is a long-felt need for an alternate method.

*Clostridium perfringens* encodes a gene for an exotoxin defined as α-toxin. The α-toxin of Cp (cpa) is reported to be the major virulence determinant of necrotic enteritis, inducing the debilitating necrotic lesions (Logan et al., 1991). *C. perfringens* type A strain is the most prevalent environmental strain and produces high levels of α-toxin (Ginter et al., 1996).

The α-toxin is a 370 amino acid (AA), zinc-dependent phospholipase C (PLC) that possesses both enzymatic and toxic properties (Justin et al., 2002). Although cpa is a phosphatidylcholine-preferring phospholipase C (PC-PLC), toxicity results from its ability to hydrolyze phosphatidylcholine and sphingomyelin phospholipid substrates, both of which are key components of eukaryotic cell membranes (Justin et al., 2002). In addition to the overt properties of hemolysis, necrosis, vascular permeabilization, and platelet aggregation, the toxin elicits a variety of subtle effects on eukaryotic cell metabolism, including activation of the arachidonic acid cascade, and stimulation of protein kinase C activity (Ginter et al., 1996).

The α-toxin consists of two domains, an α-helical N-terminal domain and an eight-stranded β-sandwich C-terminal domain. The N-terminus (AA residues 1-246) contains the phospholipase C active site and three associated zinc ion binding sites. The C-terminus (AA residues 256-370) is responsible for calcium-dependent membrane binding. Its role is to facilitate the interaction of the α-toxin with membrane phospholipids. The C-terminal domain is required for phospholipid recognition as well as for hemolytic activity of the α-toxin (Titball et al., 1999).

Fragments of the α-toxin of *Clostridium perfringens* have been produced and tested for independent function. In mice, antibodies that cross-reacted with the full-length α-toxin were induced after immunization with either the N-(Cpa1-249) or C-terminal (Cpa247-370) domain of the toxin. Smaller fragments of the α-toxin did not induce cross-reacting antibody. In vitro, anti-Cpa1-249 neutralized phospholipase C activity but not hemolytic activity of the toxin. Anti-Cpa247-370 neutralized both the phospholipase C and hemolytic activities. Of the N-terminal and C-terminal domain fragments, only immunization with Cpa247-370 induced protection against the lethal effects of the toxin in vivo. Additionally, immunization with Cpa247-370 provided protection in a mouse model against the whole organism, *C. perfringens* type A. This study confirmed the essential role of α-toxin and, specifically, the cpa C-terminal domain in the pathogenesis of gas gangrene (Williamson and Titball, 1993).

U.S. Pat. No. 5,851,827 (Titball and Williamson) relates to peptides and vaccines for inducing production of antibodies directed against *Clostridium perfringens* α-toxin in animals. Those peptides comprise the amino acid sequence of the alpha-toxin from amino acid 247 to 370 but lack the epitopes necessary for phospholipase C and/or sphingomyelin hydrolysing activity between amino acids 1 to 240. Further provided are antisera and antibodies raised to the peptides and vaccines and particularly monoclonal antibodies and hybridoma cell lines for their production.

The α-toxin produced by *Clostridium perfringens* strain NCTC 8237 was shown to differ from the α-toxins produced by most strains of *C. perfringens* isolated from human and calves at the following AA positions: Ala174 to Asp174; Thr177 to Ala177; Ser335 to Pro335. However, these differences did not alter the toxic properties of the protein. Further, a C-terminal domain vaccine derived from this strain was demonstrated to protect against the α-toxin from a bovine enteric strain of *C. perfringens* (Ginter et al., 1996).

Site-directed mutagenesis of *Clostridium perfringens* α-toxin has been the subject of numerous studies to elucidate amino acids essential for the toxic properties of this protein. Nagahama et al. (1995) reported a single point mutation in of AA H-68 or H-148 replaced with G (H68G or H148G) resulted in complete loss of hemolytic, phospholipase C, sphingomyelinase, and lethal activities of the toxin. However, antigenicity to wild type α-toxin antiserum was retained. The same outcome resulted from a H148L substitution. A H126G, H136G, or H136A mutation significantly decreased, but did not eliminate, the toxic activities. Mutation at H-46, -207, -212, or -241 showed no effect on the biological activities, indicating these residues are not essential for toxicity. Wild-type toxin and the variant toxins at H-68, -126, and -136 contained two zinc atoms. The variant toxin at H-148 possessed only one zinc atom, suggesting that H-148 tightly binds one zinc atom which is essential for the active site of α-toxin and that neither zinc atom associated with the wild type toxin is coordinated to H-68, -126, or -136.

Guillouard et al. (1996) based a series of site-directed mutagenesis studies on the crystal structure of a PC-PLC from *Bacillus cereus*, as the N-terminal domain of the *Clostridium perfringens* α-toxin is highly homologous to its complete phospholipase C. AA substitutions of D56N, H126S, H68S, H148S, H136S, E152S, H11S, or W1S resulted in significant reduction or complete elimination of biologic activities.

Also based on the known structure of *B. cereus*, Nagahama et al. (1997) investigated the role of D-56, D-130, and E-152 in hemolytic, phospholipase C (PLC), and sphingomyelinase (SMase) activities of *Clostridium perfringens* α-toxin. The replacement of D-56 in α-toxin with E, N, G, or S resulted in complete loss of hemolytic, PLC, and SMase activities. The variant toxins at D-130 showed an approximately 100-fold reduction of biological activities compared to that of the wild-type toxin. The substitution of G for E-152 caused complete loss of these activities and retained antigenicity to wild type α-toxin antiserum. However, E152Q or E152D resulted in significant but not complete elimination of toxicity.

Martin and Hergenrother (1998) studied the role of D-55 in general base catalysis by the PC-PLC from *B. cereus*, the AA position analogous to D-56 in *Clostridium perfringens* α-toxin. Substitutions were made with L, N, or E, with L resulting in the largest reduction in catalytic activity ($9 \times 10^{-5}$% of wild type).

Available *Clostridium perfringens* α-toxin (cpa) sequence is highly conserved in bovine and mammalian isolates, as determined from GenBank submissions. Many publicly available DNA sequences from chicken isolates do not extend into the C-terminal domain (GenBank Accession Numbers AAL85329, AAL85330, AAL85331, AAL85332). A full-length alpha toxin sequence from swan has been published (GenBank Accession Number AF204209) and the encoded protein is highly divergent from the alpha toxin isolated from Strain 13, a human isolate (GenBank Accession CLOPLC05) (Justin et al., 2002). Recently, full-length protein sequences of cpa from 25 chicken isolates of *C. perfringens* were compared (Sheedy et al., 2004) and found to have only small differences in amino acid sequence (one to six differences from the Strain 13 standard). These sequence variants were grouped into five types (I-V).

BRIEF SUMMARY

This invention pertains in part to the development of a vaccine for poultry against necrotic enteritis (NE). This invention utilizes exotoxin virulent factors as vaccines, after introduction of appropriate mutations to abolish their toxicity. The subject invention provides a poultry vaccine for NE. The vaccine utilizes a novel protective antigen that is a mutated, full-length, non-toxic *Clostridium perfringens* (Cp) α-toxin exotoxin (Mcpa). Utility of this vaccine was demonstrated in chickens by reduction of NE lesion severity following Cp challenge, for example.

Also disclosed herein are novel approaches for producing this vaccine in significant quantities. An exemplified approach relates to bacterial expression systems, preferably bacterial expression system utilizing *Pseudomonas fluorescens* (Pf).

A novel, Type VI alpha toxin from chicken isolates of Cp is also disclosed.

BRIEF DESCRIPTION OF THE FIGURES

Figure 1A:
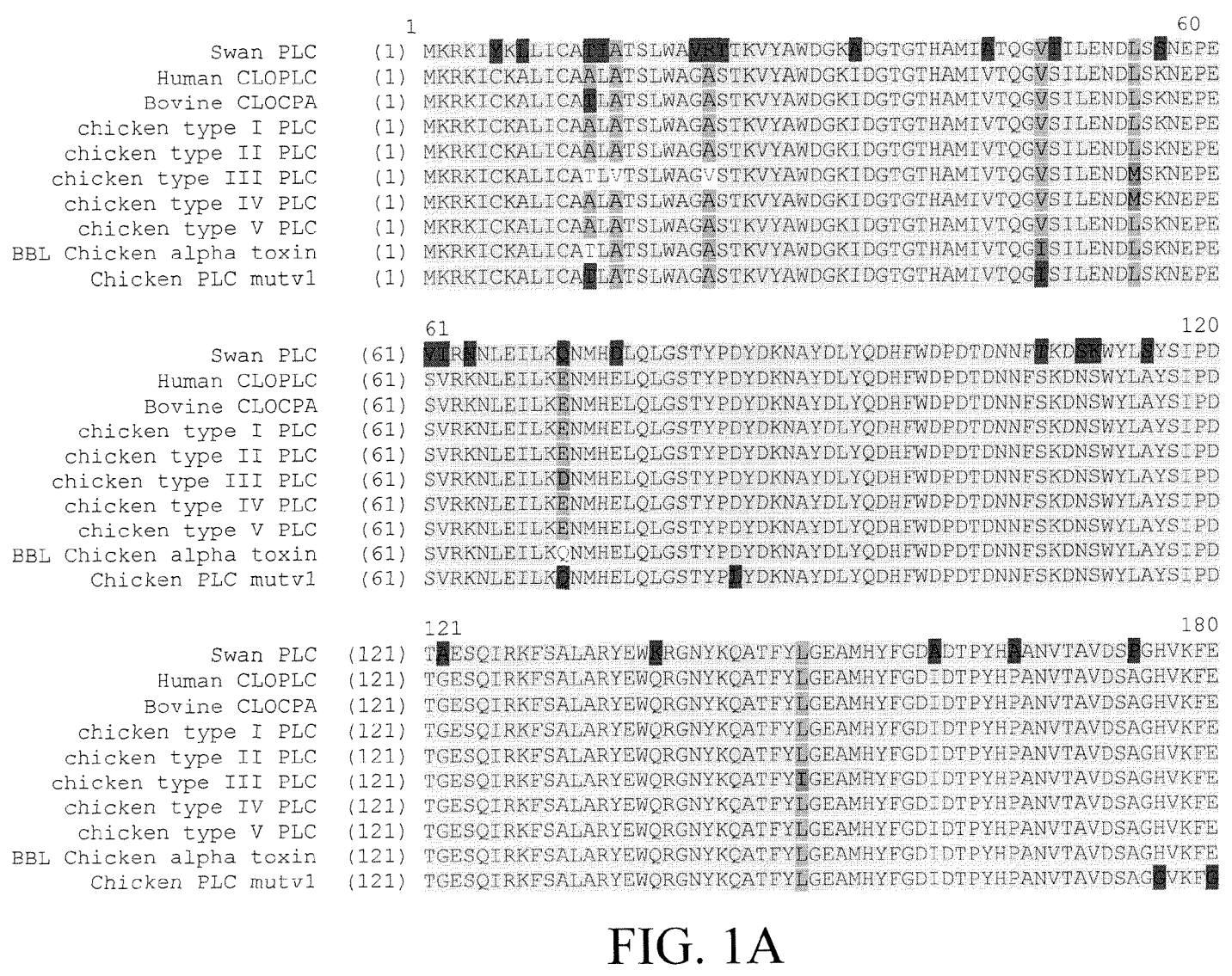

FIG. 1 shows an alignment of various *Clostridium perfringens* α-toxin amino acid sequences, isolated from chicken, swan, human, and bovine hosts.

FIG. 2 is a dendogram illustrating the sequence relatedness of chicken Cp isolates, based on deduced amino acid sequence of α-toxin.

BRIEF DESCRIPTION OF THE TABLES

Figure 3A:
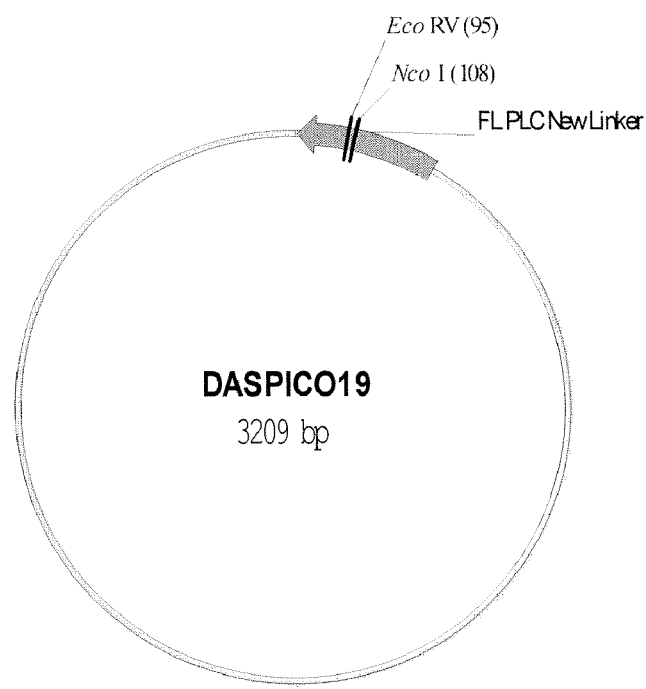
FIG. 3 illustrates cloning steps involved in constructing a vector for expression of C-terminal his-tagged Mcpa in *E. coli*.
Figure 3B:
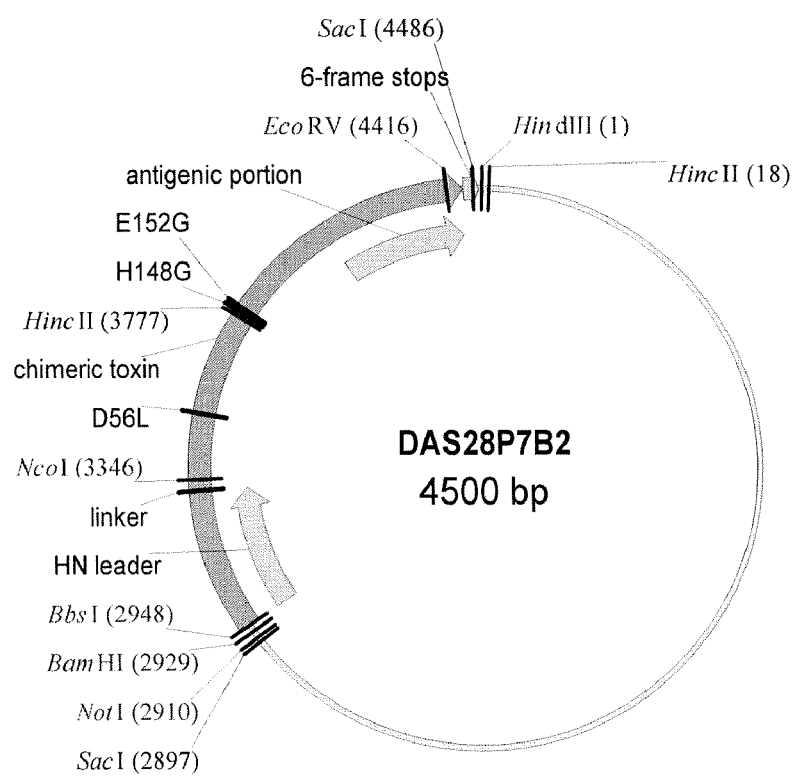
Figure 3C:
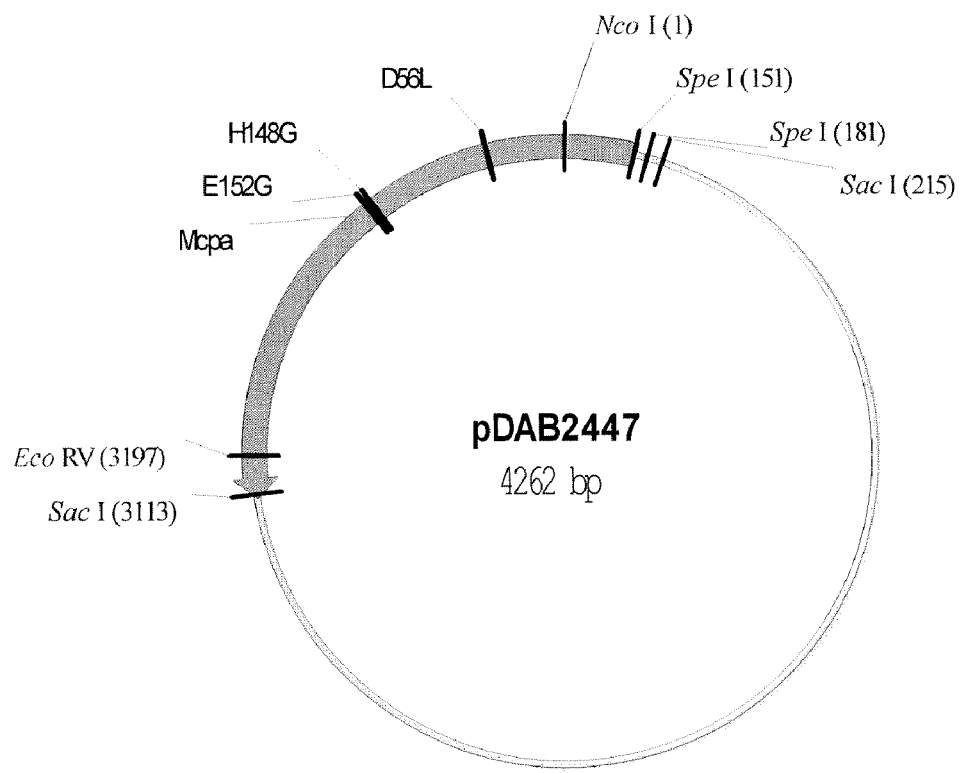
Figure 3D:
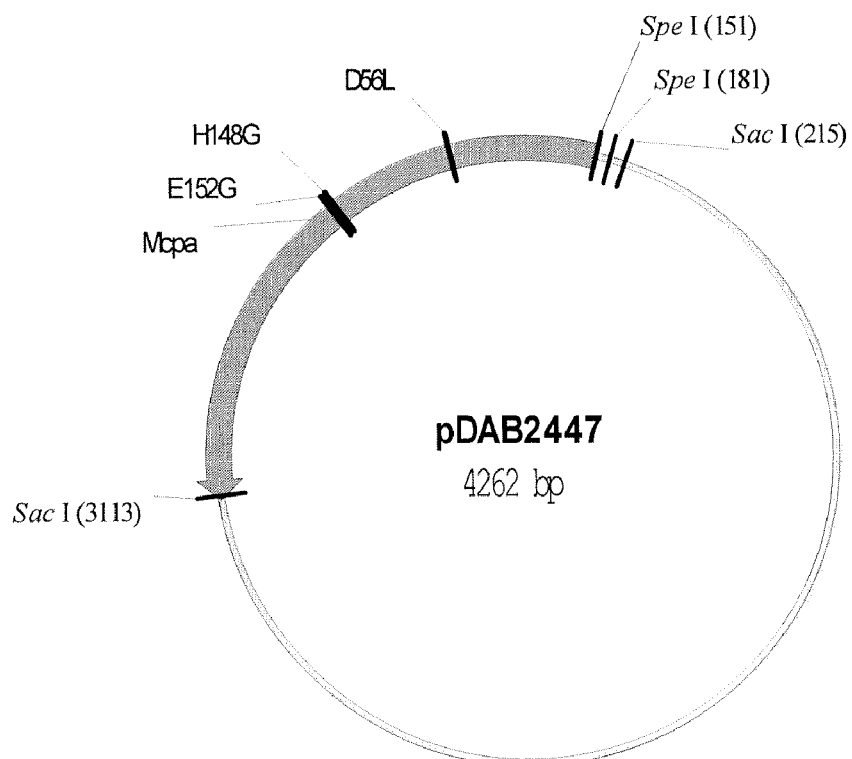
Figure 3E:
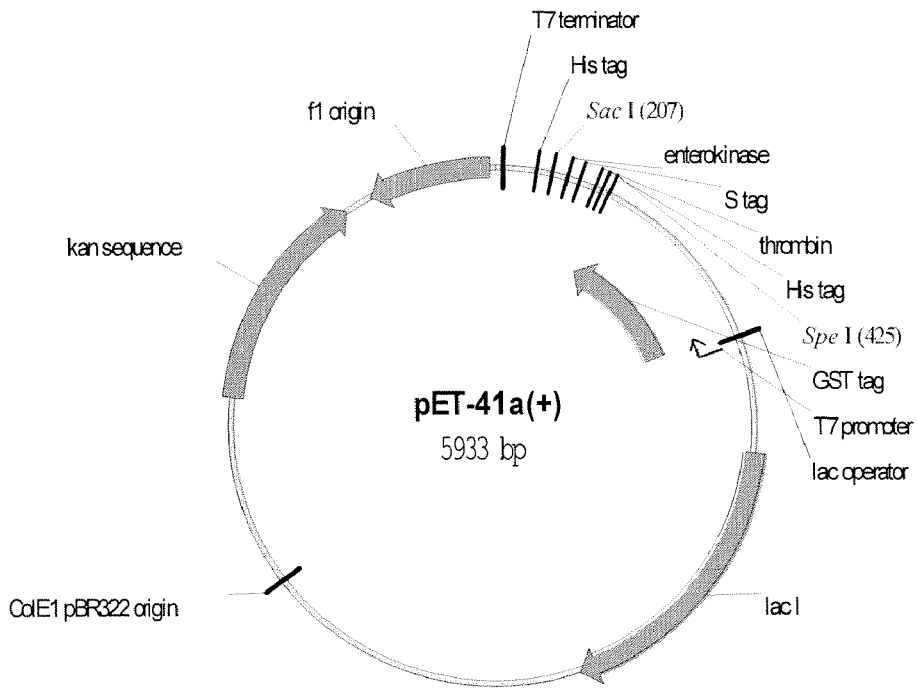
Figure 3F:
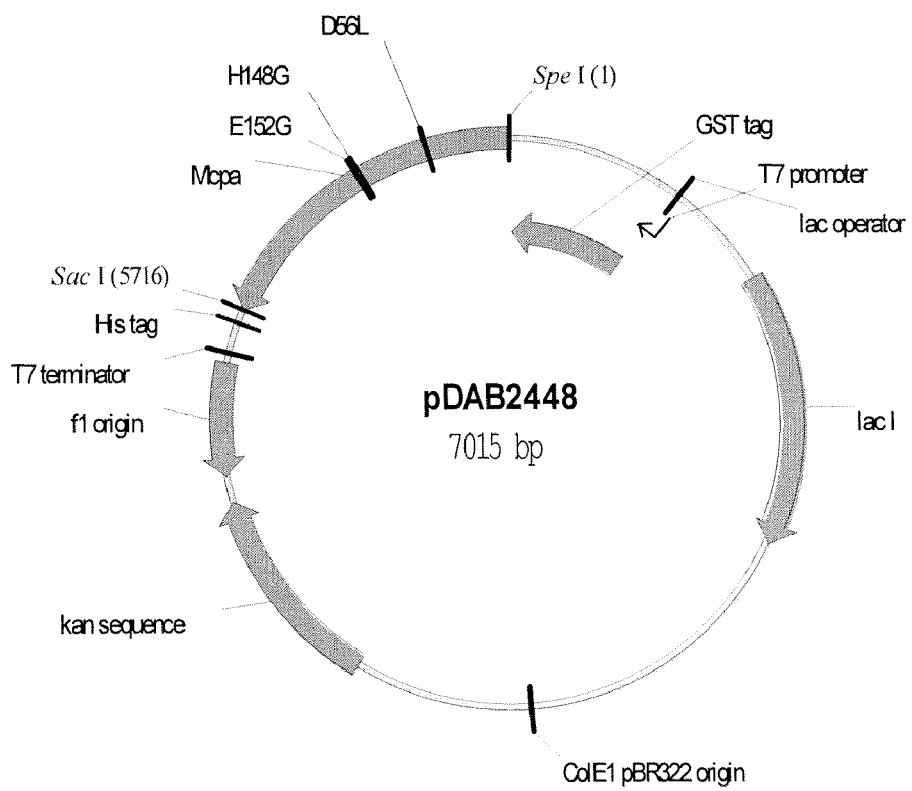

Table 1 shows variations in Cp alpha toxins isolated from chickens.

Table 2 reports values for codon bias in rice and tobacco species, as well as balanced-biased values used to design genes with optimal expression in both rice and tobacco.

Table 3 reports codon compositions of coding regions for the Mcpa protein.

Table 4 summarizes hemolytic activity endpoints of purified Mcpa samples and controls.

Table 5 outlines the clinical study design for evaluation of Mcpa antigens in young chickens.

Table 6 reports lesion scores per treatment group from the clinical trial.

Table 7 includes results of statistical analysis of lesion scores.

BRIEF DESCRIPTION OF THE SEQUENCES

SEQ ID NO:1 is the nucleotide sequence for the native alpha toxin coding region from chicken isolates of *C. perfringens*.

SEQ ID NO:2 is the native alpha toxin protein from chicken isolates of *C. perfringens* encoded by SEQ ID NO:1.

SEQ ID NO:3 is the nucleotide sequence for the plant optimized coding region for mutated mature *C. perfringens* alpha toxin.

SEQ ID NO:4 is the amino acid sequence of the mutated mature *C. perfringens* alpha toxin encoded by SEQ ID NO:3.

SEQ ID NO:5 is the plant-optimized DNA sequence for modified 15 kDa zein Endoplasmic Reticulum targeting peptide.

SEQ ID NO:6 provides the protein sequence for modified 15 kDa zein Endoplasmic Reticulum targeting peptide.

SEQ ID NO:7 provides plant-optimized DNA sequence encoding mature mutated *C. perfringens* alpha toxin protein (Mcpa) with 15 kDA zein endoplasmic reticulum targeting peptide, and KDEL ER retention peptide.

SEQ ID NO:8 provides fusion protein of mature mutated *C. perfringens* alpha toxin protein (Mcpa) with 15 kDA zein endoplasmic reticulum targeting peptide, and KDEL ER retention peptide.

SEQ ID NO:9 provides DNA sequence encoding Mcpa expressed in *Pseudomonas fluorescens* with a his-tag, thrombin recognition site, S-tag and enterokinase recognition site.

SEQ ID NO:10 provides protein sequence of Mcpa expressed in *Pseudomonas fluorescens* with a his-tag, thrombin recognition site, S-tag and enterokinase recognition site SEQ ID NO:11 provides DNA sequence encoding Mcpa expressed in *Pseudomonas fluorescens* without a his-tag, thrombin recognition site, S-tag and enterokinase recognition site.

SEQ ID NO:12 provides protein sequence of Mcpa expressed in *Pseudomonas fluorescens* without a his-tag, thrombin recognition site, S-tag and enterokinase recognition site.

SEQ ID NO:13 provides the sequence for the KDEL peptide as discussed in Example 2.

SEQ ID NO:14 is a forward primer used in Example 2.

SEQ ID NO:15 is a reverse primer used in Examples 2 and 3.

SEQ ID NO:16 is a forward primer used in Example 3.

DETAILED DESCRIPTION

This invention pertains in part to the development of a vaccine for poultry against necrotic enteritis (NE). This invention involves utilization of virulent factors such as exotoxins as vaccines after appropriate mutations to abolish their toxicity are introduced. The subject invention provides a poultry vaccine for NE. The vaccine utilizes a full-length *Clostridium perfringens* α-toxin (cpa) that is mutated. Utility of this vaccine was demonstrated by reduction of NE lesion severity in NE challenge trails.

If an α-toxin antigen could be effective for protection against poultry NE, it would require successful delivery for sensitization and subsequent neutralization of α-toxin prior to onset of necrotic lesions in the gut. It would also have to be non-toxic.

The full-length α-toxin protein was selected for evaluation according to the subject invention in an attempt to ensure proper folding and effective antigen presentation. However, a nontoxic version is required for use as a vaccine. This can be achieved by engineering multiple mutations in cpa to eliminate toxic activities and minimize the probability of reversion in a heterologous expression system. The α-toxin vaccine produced according to the subject invention was designed with 3 site-specific mutations (D56L, H148G and E152G) to abolish toxicity.

Publicly available cpa sequence is highly conserved in bovine and mammalian isolates, as determined from GenBank submissions. A full-length α-toxin sequence from swan has been published, but is highly divergent (Justin et al., 2002). Genomic DNA from two isolates of Cp derived from chicken gut was obtained (Benchmark Biolabs, Inc., Lincoln, Nebr.) and the α-toxin genes were fully sequenced. No differences were detected between the two chicken isolates. The resultant amino acid sequence was aligned with published data and determined to be highly homologous to a bovine intestinal isolate CER89L43 (see FIG. 1). FIG. 1 shows an alignment of the subject alpha toxin sequence from *Clostridium perfringens* isolates, BBL1 and BBL2 (BBL chicken alpha toxin) to the Types I-V sequences of Sheedy et al. (2004) and the swan, human, bovine, and the subject mutant cpa sequences. As illustrated in FIG. 2, the BBL gene appears to be an example of a new Type VI, most closely related to Type III. FIG. 2 is a dendogram illustrating the relatedness of the chicken Cp isolates. This new class of toxins and genes is an aspect of the subject invention.

Three amino acid positions of cpa were selected for mutation to produce a nontoxic version of cpa, while potentially retaining immunogenicity. Position 56 (aspartic acid) is a catalytic site of cpa. Two positions were selected for possible interference with zinc binding: histidine at #148 and glutamic acid at #152. Therefore, the following substitutions were made in the chicken-derived cpa sequence for use as the full-length mutated NE antigen: D56L; H148G; E152G (see FIG. 1).

Also disclosed herein is a novel approach for producing this vaccine in significant quantities. The exemplified approach relates to bacterial expression systems—preferably, a bacterial expression system utilizing the *Pseudomonas fluorescens* system described for example in U.S. Pat. No. 4,861,595.

Studies to date indicate that the mutated α-toxin protein can be expressed in significant quantities in *P. fluorescens*. The over expressed, purified protein has been tested in vitro and found not to possess hemolytic or lecithinase activities. In vivo, it has demonstrated efficacy as a vaccine. These results exemplify the use of *P. fluorescens* as a very suitable system for expressing vaccine candidate proteins. This system not only affords high level expression of animal health vaccines, but most of the protein produced is in soluble form. Yields range from 10 to 100 mg/l in shake flask depending on the type of protein; under controlled fermentor conditions these yields can be enhanced several fold making the production of vaccine cost effective and economical.

One of the objectives of this work was to generate expressed antigen to protect domesticated fowl against necrotic enteritis (NE). Thus, the subject invention relates to strategies designed to combat NE disease. One strategy, and one embodiment of the subject invention, involves producing in bacterial cultures a mutated version of a key virulence factor, Cp α-toxin, for use as a vaccine. Additionally, the purified recombinant protein can be used for applications including production of antisera (rabbit or mouse), screening monoclonals for enzyme linked immunosorbant assays (ELISA) development/optimization, and providing a positive control in Western blot development/optimization.

A full-length mutated alpha toxin (Mcpa) was tested as a vaccine candidate. To validate it as a vaccine candidate, a sufficient amount of pure protein was needed for conducting clinical studies to examine whether Mcpa provides protection against NE. To enable clinical studies and to develop reagents for evaluating the expression of NE antigens in heterologous systems, the protein was expressed in and purified from bacterial cells. Mcpa was expressed to a very high level in *E. coli* as a glutathione S-transferase (GST) fusion; however, efforts to purify Mcpa away from the GST tag using an enterokinase (EK) cleavage site were complicated due to the sensitivity of Mcpa to EK.

Therefore, Mcpa was produced in *Pseudomonas fluorescens* (Pf) with a smaller tag, purified, tested for absence of toxicity, and a sufficient quantity was obtained for clinical trials and antibody production. The Pf produced protein elicited an immune response in chickens and when administered as a subcutaneous vaccine, reduced the severity of Cp-induced NE lesions.

Additionally, a non-tagged Mcpa antigen was produced to more fully characterize the antigenic capability of the protein. Thus, the gene was modified to exclude all molecular tags. The nontagged Mcpa was expressed in *P. fluorescens*, subsequently purified, and tested for absence of toxicity. The non-tagged Mcpa also elicited an immune response in chickens and reduced the severity of NE lesions when administered as a subcutaneous vaccine.

In addition, a research project was initiated to explore the possibility of producing NE vaccine (alpha toxin) in plant cell suspension culture for commercial use in controlling NE in the poultry industry. A plant binary construct was generated to express a non-active form of the α-toxin (the zinc binding phopholipase sites were mutated via 3 single amino acid substitutions) in an effort to determine if plant-generated protein could produce an immune response to the mutated toxin. Nucleotide sequence was also redesigned to use codons for optimized expression in, preferably, rice and/or tobacco plant cells.

Successful expression in these plant systems was obtained. Although clinical testing of plant-produced antigens did not initially yield indications of efficacy, particular delivery formulations and the like could be optimized to address such issues.

A "transgenic" plant, plant cell, and the like is defined as a whole plant, plant cell, plant cell culture, plant cell line, plant tissue culture, lower plant, monocot plant cell culture, dicot plant cell culture, or progeny thereof derived from a transformed plant cell or protoplast that contains foreign DNA, introduced by laboratory techniques, not originally present in a native non-transgenic plant cell of the same species. The terms "transgenic plant" and "transformed plant" have sometimes been used in the art as synonymous terms to define a plant whose DNA contains an exogenous DNA molecule. A transgenic plant may be stably transformed to contain foreign DNA that functions within, and is incorporated into, the genomic DNA of the plant or is a transgenic plant which has been transformed by viral-based vectors and transiently expressed the foreign DNA.

For practice of the present invention, it can be preferable to transform plant cell lines that can be cultured and scaled-up rapidly. The use of plant cell cultures avoids open field production and greatly reduces the chances of gene escape and food contamination. Tobacco suspension cell cultures such NT-1 and BY-2 (Kato et al. 1972, Proc. IV IFS: Ferment. Technol. Today 689-695; An, G., 1985 *Plant Physiol.* 79, 568-570; Nagata et al. 1992, International Review of Cytology 132, 1-30.) are some preferred embodiments because these lines are particularly susceptible to handling in culture, are readily transformed, produce stably integrated events, and are amenable to cryopreservation.

Thus, the tobacco suspension cell line, NT-1, is suitable for the practice of the present invention. NT-1 cells were originally developed from *Nicotiana tabacum* L.cv. bright yellow 2. The NT-1 cell line is widely used and readily available; though, almost any suspension cell line (tobacco or otherwise) can be used to practice the invention. Moreover, the cell line is variable and will change in response to culture conditions. NT-1 cells suitable for use are available from the American Type Culture Collection under accession number ATCC No. 74840. See also U.S. Pat. No. 6,140,075.

Plant cell cultures for producing the subject vaccines can contain transformed plant cell lines derived from a lower plant, a dicotyledonous plant, or a monocotyledonous plant. Non-limiting examples of dicotyledonous plants from which the transformed cell lines can be derived are tomato, potato, sweet potato, cassava, legumes including alfalfa and soybean, carrot, strawberry, lettuce, oak, maple, walnut, rose, mint, sunflower, safflower, cotton, tobacco, squash, daisy, canola or cactus. Some preferred lines include tobacco cells lines such as NT-1 or BY-2. Where the transformed plant cell line is derived from a monocotyledonous plant, plants such as wheat, turf, turf grass, cereal, maize or corn, rice, oat, wheat, barley, sorghum, orchid, iris, lily, onion, banana, sugarcane, sorghum, or palm can be used to establish the plant cell line. Additionally, cell lines can be established from lower plants such as ferns, gymnosperms, conifers, horsetails, club mosses, liver warts, hornworts, mosses, red algaes, brown algaes, gametophytes, sporophytes of pteridophytes, or green algae. Some preferred plant cell cultures can be derived from corn, rice or tobacco plants.

Construction of gene cassettes for transforming plants or transformed plant cell cultures can readily be accomplished by utilizing well known methods, such as those disclosed in Sambrook et al. (1989); and Ausubel et al., (1987) *Current Protocols in Molecular Biology*, John Wiley and Sons, New York, N.Y.

After preparing a stably transformed plant cell line, the cultures may be finished by confirming the gene insert (genetic event) using PCR amplification of the whole gene insert followed by restriction enzyme digestion. Media for agar plates and suspension cultures can be based on common plant culture media (Murashige and Skoog; MS).

Thus, the subject invention includes plant cell cultures and methods of culturing and storing plant cells for the production of NE vaccines. Other aspects of the invention provide a plant-cell-produced vaccine production system.

Poultry is herein defined as any domesticated bird kept for eggs or meat, especially chicken, turkey, and ostrich.

"Isolated" and "purified" imply the "hand of man" and can apply to polynucleotides and proteins. A cloned polynucleotide is an isolated polynucleotide, for example.

A vaccine is a composition used to vaccinate an animal that contains at least one proteinaceous agent that induces the stimulation of the host immune system and prevents or attenuates subsequent unwanted pathology associated with the host reactions to subsequent exposures of the pathogen.

A pathogenic organism is a bacterium, virus, fungus, or protozoan that causes a disease or induced/controlled physiologic condition in an animal or host that it has infected.

An adjuvant is a substance that accentuates, increases, moderates or enhances the immune response to an immunogen or antigen. Adjuvants typically enhance both the humoral and cellular immune response but an increased response to either in the absence of the other qualifies to define an adjuvant. Moreover, adjuvants and their uses are well known to immunologists and are typically employed to enhance the immune response when doses of immunogen are limited, when the immunogen is poorly immunogenic, or when the route of administration is sub-optimal. Thus the term "adjuvanting amount" is that quantity of adjuvant capable of enhancing the immune response to a given immunogen or antigen. The mass that equals an "adjuvanting amount" will vary and is dependent on a variety of factors including, but not limited to, the characteristics of the immunogen, the quantity of immunogen administered, the host species, the route of administration, and the protocol for administering the immunogen. The "adjuvanting amount" can readily be quantified by routine experimentation given a particular set of circumstances. This is well within the ordinarily skilled artisan's purview and typically employs the use of routine dose response determinations to varying amounts of administered immunogen and adjuvant. Responses are measured by determining serum antibody titers or cell-mediated responses raised to the immunogen using enzyme linked immunosorbant assays, radio immune assays, hemagglutination assays and the like.

An "effective dosage" is an amount necessary to induce an immune response in an animal sufficient for the animal to effectively resist a challenge mounted by a pathogenic agent. The dosages administered to such animal will be determined by a physician, veterinarian, or trained scientist in the light of the relevant circumstances including the particular immunoprotective particle or combination of particles, the condition and size of the animal, and the chosen route of administration. Some effective dosages are in the Examples below.

Polynucleotides of the subject invention can be modified to have codon usage that is optimized for expression in various heterologous systems. Such techniques are well-known in the art. See, e.g., U.S. Pat. Nos. 6,013,523 and 6,015,891. The Mcpa gene disclosed herein was codon-optimized for expression in tobacco or rice plant cell culture. Surprisingly, the same nucleotide sequence resulted in a high yield in *E. coli* and *P. fluorescens*. *P. fluorescens* is the preferred expression system for recovery of soluble Mcpa antigen.

The present invention also includes DNA sequences having substantial sequence homology with the disclosed sequences encoding immunoprotective antigens. As used in the present application, the term "substantial sequence homology" is used to indicate that a nucleotide sequence (in the case of DNA or RNA) or an amino acid sequence (in the case of a protein or polypeptide) exhibits substantial, functional or structural equivalence with another nucleotide or amino acid sequence. Any functional or structural differences between sequences having substantial sequence homology, identity, or similarity will be de minimis; that is, they will not affect the ability of the sequence to function as indicated in the present application. Sequences that have substantial sequence homology with the sequences disclosed herein are usually variants of the disclosed sequence, such as mutations, but may also be synthetic sequences.

Embodiments of the subject invention can include variants having 90, 91, 92, 93, and 94% identity, and more preferably those having 95, 96, 97, 98, and 99% identity with an exemplified sequence, and that function as substantial equivalents. These changes, including conservative and/or in some cases nonconservative changes, are in parts of these sequences that are not critical to the functionality. Exemplary techniques for modifying oligonucleotide sequences include using polynucleotide-mediated, site-directed mutagenesis, are described in, for example, Zoller et al. (1984); Higuchi et al. (1988); Ho et al. (1989); Horton et al. (1989); and *PCR Technology: Principles and Applications for DNA Amplification*, (ed.) Erlich (1989).

The use of genetic engineering techniques is well known in the art. Appropriately reconstructing the gene and appropriately positioning it in a host plasmid vector between a promoter, possibly a strong regulated promoter, and transcription/translation terminators, can accomplish the expression of the Mcpa in a particular foreign host. The suitability of any such host can also be tested by means known to one of ordinary skill in the art.

Once the transformed microbial cells (preferably *Pseudomonas fluorescens*) have expressed the Mcpa to a desired (generally a high) level, the cells can be harvested, lysed, purified, and formulated with adjuvant. In this aspect of the invention, compositions containing purified recombinant proteins are prepared and can be administered in amounts sufficient to induce a desired biological effect.

The subject invention provides active Mcpa compositions, including those wherein the Mcpa was produced in microbial systems. Cells of the subject invention can be delivered by oral, nasal, ocular or parental injection means. Such methods of inoculation can also be used to treat non-bird animals, as well. Methods of the subject invention can also be used for curtailing NE. Such vaccines can be enhanced by an adjuvant and/or accelerant of the immune response via the administration of the purified recombinant protein and the adjuvant in amounts sufficient to induce a desired biological effect.

Microbial cells suitable for use in the subject invention include prokaryotes (both Gram positive and Gram negative organisms) and lower eukaryotes, such as fungi. Species of bacterial cells suitable for use in the instant invention include those of the genera: 1) Enterobacteriaceae, including the species of the genera *Escherichia, Erwinia, Shigella, Salmonella*, and *Proteus;* 2) Bacillaceae; 3) Rhizobiaceae, such as *Rhizobium;* 4) Spirillaceae, such as *photobacterium, Zymomonas, Serratia, Aeromonas, Vibrio, Desulfovibrio, Spirillum;* 6) Lactobacillaceae; 7) Pseudomonadaceae, such as *Pseudomonas* and *Acetobacter;* 8) Azotobacteraceae and Nitrobacteraceae. Other suitable organisms include lower eukaryotes, fungi (such as Phycomycetes and Ascomycetes), yeast (such as *Saccharomyces* and *Schizosaccharomyces*), Basidiomycetes yeast (such as *Rhodotorula, Aureobasidium, Sporobolomyces*), and the like.

The cellular host containing one or more heterologous genes may be grown in any convenient nutrient medium, where the DNA construct provides a selective advantage (e.g., growth in a selective medium containing antibiotics), providing for a selective medium so that substantially all or all of the cells retain the heterologous gene(s). These cells may then be harvested in accordance with conventional ways.

Various constructs may be used, which include replication systems from plasmids, viruses, or centromeres in combination with autonomous replicating segments (ars) for stable maintenance. Where only integration is desired, constructs can be used which may provide for replication, and are either transposons or have transposon-like insertion activity or provide for homology with the genome of the host. Frequently, DNA sequences are employed having the heterologous gene between sequences which are homologous with sequences in the genome of the host, either chromosomal or plasmid. The heterologous gene(s) can be present in multiple copies. See for example, U.S. Pat. No. 4,399,216. Thus, conjugation, transduction, transfection and transformation may be employed for introduction of the heterologous gene.

In embodiments where an extrachromosomal element is employed, the DNA construct will desirably include a marker that allows for a selection of those host cells containing the construct. The marker is commonly one which provides for biocide resistance, e.g., antibiotic resistance or heavy metal resistance, complementation providing prototrophy to an auxotrophic host, or the like. The replication systems can provide special properties, such as runaway replication, can involve cos cells, or other special features.

Heterologous gene(s), having transcriptional and translational initiation and termination regulatory signals recognized by the host cell, can be employed in conjunction with the heterologous gene. The DNA sequence can be manipulated so that a transcriptional initiation regulatory sequence is provided that is different from the natural one.

A wide variety of transcriptional initiation sequences exist for a wide variety of hosts. The sequence can provide for constitutive expression of the Mcpa gene or regulated expression, where the regulation may be inducible by a chemical, e.g., a metabolite, by temperature, or by a regulatable repressor. See for example, U.S. Pat. No. 4,374,927. The particular choice of the promoter will depend on a number of factors, the strength of the promoter, the interference of the promoter with the viability of the cells, the effect of regulatory mechanisms endogenous to the cell on the promoter, and the like. A large number of promoters are available from a variety of sources, including commercial sources.

Vectors suitable for expression of the Mcpa are known to those skilled in the art. Likewise, heterologous genes encoding native cpa's are known to those skilled in the art. Polypeptide sequences and coding sequences may be obtained from a variety of sources including various patent databases and other publicly available databases (such as the nucleic acid and protein databases found at the National Library of Medicine or the European Molecular Biology Laboratory). In some aspects of the subject invention, microbial cells are manipulated to express various combinations of cpa's.

The subject invention provides methods of inducing and/or accelerating an immune response in an individual comprising the steps of administering to a poultry animal a composition comprising purified Mcpa and one or more adjuvanting molecules in an amount effective to engender an immune response in said animal.

The subject invention provides methods for the stimulation and/or modulation of the immune system of a poultry animal wherein said method comprises administration of a composition comprising Mcpa protein expressed according to the teachings of the subject invention.

In other embodiments, the subject invention includes compositions containing a (at least one) novel Mcpa of the subject invention, which modulate a desired biological effect. Such compositions are administered in amounts effective to stimulate, modulate, affect, or produce a desired biological effect (e.g., bacterial resistance).

The desired biological effect can be selected from, for example, the group consisting of: 1) activation or stimulation of macrophage in an individual; 2) stimulation or modulation of the immune system of an individual; and 3) increasing bacterial resistance in an individual.

Thus, the subject invention provides a number of non-limiting embodiments and aspects that include:

Vaccine comprising protein derived from one or more heterologous genes encoding a modified protective antigen against a C. perfringens alpha-toxin (Mcpa);

said vaccine, wherein the heterologous gene(s) are contained in a single vector;

said vaccine, wherein the heterologous genes are contained in multiple vectors;

said vaccine, wherein the microbial cell is Gram positive, Gram negative organisms, or a lower eukaryote, such as fungi;

said vaccine, wherein the microbial expression system is Pseudomonas fluorescens.

The subject invention also includes a method of inducing and/or accelerating an immune response in an individual poultry animal, including an individual in a plurality of poultry animals, to an antigen or immunogen comprising the steps of administering, to said individual:

a vaccine comprising one or more heterologous genes encoding an Mcpa;

and optionally, a lipopolysaccharide (LPS), for example, in an amount effective to engender an immune response.

Still further embodiments of the subject invention can be used to prevent NE in poultry animals (such as chickens), including protecting newborn, adolescent, and adult chickens from the onset of said disease or disease symptoms.

Compositions of the subject invention can be administered orally, parenterally, as sprays (including inhalation sprays), topically, rectally, nasally, buccally, vaginally, or via an implanted reservoir. The term parenteral, as used herein, includes subcutaneous, intradermal, intravenous, intrastriatial, intramuscular, intraperitoneal, intrathecal, intraventricular, intrasternal, or intracranial injection and other infusion techniques. Compositions can be formulated in any suitable carriers, including for example, carriers described in E. W. Martin's *Remington's Pharmaceutical Science*, Mack Publishing Company, Easton, Pa.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Abbreviations Used: SDS-PAGE, sodium dodecyl sulfate polyacrylamide gel electrophoresis; dI, deionized; DTT, dithiothreitol; TRIS, tris(hydroxymethyl) aminomethane hydrochloride; MWCO, molecular weight cut off; bp, base pairs; TAE, Tris Acetate EDTA, MSG, monosodium glutamate; CV, column volume; PBS, phosphate buffer saline

EXAMPLES

Example 1

Cloning and Sequencing of a Full-Length Alpha Toxin (cpa) Gene from *C. perfringens* Isolates Derived from Chickens This example describes the isolation and base sequence determination of DNA fragments containing overlapping portions of a gene encoding an alpha toxin protein (cpa) from two strains of *Clostridium perfringens*. These strains (BBL1 and BBL2) were isolated at Benchmark BioLabs (Lincoln, Nebr.) from the gut of chickens diagnosed with naturally occurring necrotic enteritis. The two isolates came from different birds of the same flock and had different characteristics when grown in the laboratory (e.g. differed in the amount of cpa they secreted in culture filtrates).

Genomic DNA was prepared from cells of BBL1 and BBL2 and used as the template for Polymerase Chain Reactions (PCR) to amplify overlapping fragments of the cpa gene. Primer sequences were designed from the DNA sequences of the highly conserved cpa genes from human isolates of *C. perfringens* (GenBank Accession Numbers CLOPLC, CLOPLC05 and NC_003366). Primer pairs were chosen to amplify overlapping fragments which together contained the DNA sequence of the entire cpa protein coding region and a small amount of 5' and 3' flanking sequences. Primer Pair One consisted of Forward Primer PLC 5'FS (5'-GGTATAATTTCAGTGCAAGTGTTAATCGTTATC-3') and Reverse Primer PLC INTR1 (5'-CCATC-CTTTGTTTTGATTCCAAAATAC-3') and produced an amplification product of 1019 base pairs. Primer Pair Two consisted of Forward Primer PLC INTF1 (5'-GAAAATTTTCAGCATTAGCTAGATATGAATGG-3') and Reverse Primer PLC 3'R (5'-AGCTTTTATTTTGTAAATAC-CACCAAAACC-3') and produced an amplification product of 869 base pairs. The two amplification products overlapped by 558 base pairs. PCR reactions contained (final volume of 25 μL) 214 ng (BBL1) or 275 ng (BBL2) of DNA template, 50 pmol each of the appropriate Forward and Reverse Primers, 1× FailSafe™ Buffer D (Epicentre®, Madison, Wis.), and 1.25 units of FailSafe™ Enzyme Mix. Amplification occurred during 20 cycles of: 96°, 30 sec; 45°, 30 sec; 72°, 30 sec; followed by extension for 10 minutes at 72°. The PCR products were cloned into the TOPO TA 2.1 vector as directed by the supplier's instructions (Invitrogen, Carlsbad, Calif.) and transformed by standard methods into *Escherichia coli* (*E. coli*) Top10 cells (Invitrogen). Insert sizes of recombinant plasmids prepared from individual colonies were analyzed by restriction enzyme digestion and plasmids from clones having the appropriate sized inserts were prepared for DNA sequence analysis. DNA sequences of the inserts from a clone of each amplification product from each strain were determined by Dye Terminator Cycle Sequencing Quick Start Master Mix according to the supplier's recommendations (Beckman Coulter, Inc., Fullerton, Calif.). The overlapping sequences from each strain were assembled into a single DNA sequence containing an uninterrupted open reading frame (ORF) that encodes an alpha toxin (cpa) protein. Comparison of the DNA sequences of the cpa ORFs from BBL1 and BBL2 showed that they were identical, (SEQ ID NO:1) and thus encoded identical proteins (SEQ ID NO:2). The 398 amino acid alpha protoxin protein from these BBL strains constitutes a new class (Type VI) of chicken alpha toxins, as summarized in Table 1. Table 1 shows the amino acid (AA)

residues present at the variant positions of the alpha toxin proteins; all other amino acids are identical in the 7 proteins examined.

In accordance with results of studies of alpha toxin proteins of other *C. perfringens* isolates, it is predicted that the first 28 amino acid residues of SEQ ID NO:2 constitute a secretion signal peptide that is removed during secretion of the protoxin from the bacterial cell, and that the mature alpha toxin comprises amino acids 29-398 of SEQ ID NO:2 (370 amino acids).

Example 2

Design and Synthesis of a Mutated Full-Length Alpha Toxin (Mcpa) Gene for Expression in Plant Cells Optimization of sequence for expression in plants. To obtain high expression of heterologous genes in plants it may be preferred to reengineer said genes so that they are more efficiently expressed in plant cells. Rice and tobacco are two such plants where it may be preferred to redesign the heterologous gene(s) prior to transformation to increase the expression level (i.e. produce more protein) in a transgenic plant cell. Therefore, a step in the design of genes encoding a bacterial alpha toxin for plant expression (i.e., in addition to the provision of plant gene promoter elements, introns, 3' untranslated regions, etc.) is reengineering of a heterologous gene protein coding region for optimal expression.

One impetus for the reengineering of a bacterial alpha toxin coding sequence for expression in plant cells is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the protein coding DNA of genes introduced into plants (e.g., TATA box regions normally found in plant gene promoters) may result in aberrant transcription of the genes. On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Extensive analysis of the 1197 base pairs (bp) of the DNA sequence of the native *C. perfringens* alpha toxin coding region disclosed herein as SEQ ID NO. 1 revealed the presence of several sequence motifs that are thought to be detrimental to optimal plant expression, as well as a non-optimal codon composition. Thus, one goal in the design of plant optimized gene(s) encoding a bacterial alpha toxin is to generate a DNA sequence that is more "plant-like" in nature, and in which the sequence modifications do not hinder translation or create mRNA instability.

Multiple publicly available DNA sequence databases exist wherein one may find information about the G+C contents of plant genomes or the protein coding regions of various plant genes. One such database is located on the World Wide Web at the URL http://www.kazusa.or.jp/codon/. At this site, one may find that the average G+C content of tobacco (*Nicotiana tabacum*) protein coding sequences is 43.3% (analysis of 1268 sequences comprising 453,797 codons). One may also find that the average G+C content of rice (*Oryza sativa* japonica cultivar) protein coding sequences is 55% (analysis of 32,630 sequences comprising 12,783,238 codons). In comparison, the G+C content of the *C. perfringens* alpha toxin protein coding sequence disclosed in SEQ ID NO:1 is 33.3%.

Thus, it may be advantageous when designing an alpha toxin gene for expression in rice or tobacco cells to raise the G+C content of the protein coding region to a range of 40-55%. Therefore, one goal in the design of genes encoding a bacterial toxin for plant expression, more preferably referred to as plant optimized gene(s), is to generate a DNA sequence having a G+C content preferably close to that of native host plant genes coding for metabolic enzymes.

Due to the plasticity afforded by the redundancy/degeneracy of the genetic code (i.e., some amino acids are specified by more than one codon), evolution of the genomes in different organisms or classes of organisms has resulted in differential usage of synonymous codons. This "codon bias" is reflected in the mean base composition of protein coding regions. For example, organisms having genomes with relatively low G+C contents utilize more codons having A or T in the third position of synonymous codons, whereas those having higher G+C contents utilize more codons having G or C in the third position. For example, it is found that in tobacco coding regions, G or C is found as the third base of 39.84% of codons, while in rice coding regions, G or C is found as the third letter of 61.29% of codons. Further, it is thought that the presence of "minor" codons within an mRNA may reduce the absolute translation rate of that mRNA, especially when the relative abundance of the charged tRNA corresponding to the minor codon is low. An extension of this reasoning is that the diminution of translation rate by individual minor codons would be at least additive for multiple minor codons. Therefore, mRNAs having high relative contents of minor codons would have correspondingly low translation rates. This rate would be reflected by correspondingly low levels of the encoded protein.

In engineering genes encoding a bacterial alpha toxin for expression in rice or tobacco (or other plants, such as maize, cotton or soybean), it is helpful if the codon bias of the prospective host plant(s) has been determined. The codon bias is the statistical distribution of codons that the plant uses for coding the amino acids of its proteins, and the preferred codon usages for rice and tobacco are shown in Table 2. The codon bias can be calculated as the frequency at which a single codon is used relative to the codons for all amino acids. Alternatively, the codon bias may be calculated as the frequency at which a single codon is used to encode a particular amino acid, relative to all the other codons for that amino acid (synonymous codons). In designing coding regions for plant expression of bacterial alpha toxins, the primary ("first choice") codons preferred by the plant should be determined, as well as the second, third, fourth etc. choices of preferred codons when multiple choices exist. A new DNA sequence can then be designed which encodes the amino sequence of the bacterial alpha toxin, but the new DNA sequence differs from the native bacterial DNA sequence (encoding the toxin) by the substitution of plant (first preferred, second preferred, third preferred, or fourth preferred, etc.) codons to specify the amino acid at each position within the toxin amino acid sequence. The new sequence is then analyzed for restriction enzyme sites that might have been created by the modifications. The identified sites are further modified by replacing the codons with first, second, third, or fourth choice preferred codons. Other sites in the sequence which could affect transcription or translation of the gene of interest are the exon: intron junctions (5' or 3'), poly A addition signals, or RNA polymerase termination signals. The sequence is further analyzed and modified to reduce the frequency of TA or GC doublets. In addition to the doublets, G or C sequence blocks that have more than about six residues that are the same can affect transcription or translation of the sequence. Therefore, these blocks are advantageously modified by replacing the codons of first or second choice, etc. with the next preferred codon of choice.

The method described above enables one skilled in the art to modify gene(s) that are foreign to a particular plant so that the genes are optimally expressed in plants. The method is further illustrated in PCT application WO 97/13402. Thus, synthetic genes that are functionally equivalent to the toxins/genes of the subject invention can be used to transform hosts, including plants. Additional guidance regarding the production of synthetic genes can be found in, for example, U.S. Pat. No. 5,380,831.

To engineer a plant-optimized gene encoding a bacterial alpha toxin, a DNA sequence was designed to encode the amino acid sequence of the protein toxin, utilizing a redundant genetic code established from a codon bias table compiled from the protein coding sequences for the particular host plants (rice and tobacco). In Table 2, Columns C, D, I, and J present the distributions (in % of usage for all codons for that amino acid) of synonymous codons for each amino acid, as found in the coding regions of Oryza sativa (rice) and Nicotiana tabacum (tobacco) genes. The codons most preferred by each plant type are indicated in bold font, and the second, third, or fourth choices of codons can be identified when multiple choices exist. It is evident that some synonymous codons for some amino acids are found only rarely in plant genes (e.g. TTA in rice and GCG in tobacco). Also, rice and tobacco plants differ in codon usage (e.g. Alanine codon GCC occurs more frequently in rice genes than in tobacco genes, while Arginine codon AGA is more often used in tobacco genes than in rice genes). Thus, it is obvious that a protein coding region designed to reflect the optimal codon composition of genes of one plant species may have a suboptimal codon composition for expression in another plant species. Therefore, in the design process of creating a protein-encoding DNA sequence that approximates an average codon distribution of both rice and tobacco genes, any codon that is used infrequently relative to the other synonymous codons for that amino acid in either type of plant was excluded (indicated by DNU in Columns F and L of Table 2). Usually, a codon was considered to be rarely used if it is represented at about 10% or less of the time to encode the relevant amino acid in genes of either plant type (indicated by NA in Columns E and K of Table 2). To balance the distribution of the remaining codon choices for an amino acid, a Weighted Average representation for each codon was calculated, using the formula:

Weighted Average % of $C1=1/(\% C1+\% C2+\% C3+\text{etc.})\times \% C1\times 100$ where C1 is the codon in question and % C2, % C3, etc. represent the averages of the % values for rice and tobacco of remaining synonymous codons (average % values for the relevant codons are taken from Columns E and K) of Table 2.

The Weighted Average % value for each codon is given in Columns F and L of Table 2.

A new DNA sequence which encodes essentially the amino acid sequence of the C. perfringens alpha toxin protein of SEQ ID NO:2 was designed for optimal expression in both rice and tobacco cells using a balanced codon distribution of frequently used codons found in rice and tobacco genes. As mentioned above, the first 28 amino acids of the protoxin sequence disclosed in SEQ ID NO:2 comprise a secretion signal peptide. Accordingly, a plant-optimized DNA sequence (SEQ ID NO:3) was designed to encode only the mature protein portion of SEQ ID NO:2 (amino acids 29-398) but which had been modified to contain three amino acid changes to remove phospholipase C enzymatic activity, as discussed above and disclosed in SEQ ID NO:4. These changes are summarized below:

Aspartic Acid 84 of protoxin (residue 56 of mature protein) mutated to Leucine

Histidine 176 of protoxin (residue 148 of mature protein) mutated to Glycine

Glutamic Acid 180 (residue 152 of mature protein) mutated to Glycine

The new DNA sequence differs from the native bacterial DNA sequence encoding the alpha toxin protein by the substitution of plant (first preferred, second preferred, third preferred, or fourth preferred) codons to specify the appropriate amino acid at each position within the protein amino acid sequence. Design of the plant-optimized DNA sequence was initiated by reverse-translation of the protein sequence of SEQ ID NO:4 using a balanced rice-tobacco codon bias table constructed from Table 2 Columns F and L. The initial sequence was then modified by compensating codon changes (while retaining overall weighted average codon representation) to remove or add restriction enzyme recognition sites, remove highly stable intrastrand secondary structures, and remove other sequences that might be detrimental to cloning manipulations or expression of the engineered gene in plants. The DNA sequence was then re-analyzed for restriction enzyme recognition sites that might have been created by the modifications. The identified sites were further modified by replacing the relevant codons with first, second, third, or fourth choice preferred codons. Other sites in the sequence which could affect transcription or translation of the gene of interest include the exon:intron junctions (5' or 3'), poly A addition signals, or RNA polymerase termination signals. The modified sequence was further analyzed and further modified to reduce the frequency of TA or CG doublets, and to increase the frequency of TG or CT doublets. In addition to these doublets, sequence blocks that have more than about six consecutive residues of [G+C] or [A+T] can affect transcription or translation of the sequence. Therefore, these sequence blocks were also modified by replacing the codons of first or second choice, etc. with other preferred codons of choice. Rarely used codons are not included to a substantial extent in the gene design, being used only when necessary to accommodate a different design criterion than codon composition per se (e.g. addition or deletion of restriction enzyme recognition sites).

The resulting DNA sequence has a higher degree of codon diversity, a desirable base composition, contains strategically placed restriction enzyme recognition sites, and lacks sequences that might interfere with transcription of the gene, or translation of the product mRNA. Table 3 presents a comparison of the codon compositions of the coding regions for the mature alpha toxin protein as found in the native gene and the plant-optimized version, and compares both to the codon composition recommendations for a plant optimized sequence as calculated from Table 2 Columns F and L.

Other modifications to the plant-optimized sequence encoding the mature C. perfringens alpha toxin were made. One such modification was the addition of a DNA sequence encoding the endoplasmic reticulum (ER) targeting peptide derived from the maize (Zea mays) 15 kDa alpha zein gene (Genbank Accession Number M72708). This DNA sequence comprises 63 bases, and has been modified from the original maize sequence by codon substitutions to make its composition more compatible with expression in rice and tobacco cells (as described above) and by the addition of a GCT codon for Alanine immediately following the ATG (Methionine) start codon. The addition of this GCT codon places the ATG translational start codon in a sequence context that is favorable for translation initiation in plants. The rice-tobacco optimized DNA sequence for the 15 kDa zein ER targeting peptide is disclosed as SEQ ID NO:5, and the encoded peptide is disclosed as SEQ ID NO:6. When the DNA sequence of SEQ ID NO:5 is placed at the beginning of the DNA sequence of SEQ ID NO:3, a full length reading frame of 1239 bases is created that encodes a fusion protein comprising the 15 kDa zein ER targeting peptide linked to the C. perfringens alpha toxin mature protein. When this reading frame is introduced into plant cells as a functional gene, the protein translated from the mRNA will be directed into the lumen of the endoplasmic reticulum. It is known in the art that, after entering the ER, heterologous proteins are often secreted from the cell. It is further known that certain small peptide sequences, when added to the carboxy-terminus of proteins directed to the ER, can inhibit the secretion of the thus modified proteins from the cell. Since it is an object of this invention to accumulate high levels of the mutated C. perfringens alpha toxin protein in rice and tobacco cells, a further modification to the DNA disclosed in SEQ ID NO:3 was the addition of codons encoding a KDEL (Lysine-Aspartic Acid-Glutamic Acid-Leucine) (SEQ ID NO:13) peptide (known to facilitate retention of proteins within the ER) to the 3' end of the sequence. In practice, since the mature C. perfringens alpha toxin protein disclosed in SEQ ID NO:4 terminates in Lysine, only codons specifying DEL (i.e. GATGAGCTT) were added to SEQ ID NO:3. The full length, plant-optimized DNA sequence encoding this fusion protein is disclosed in SEQ ID NO:7, and the encoded fusion protein is disclosed in SEQ ID NO:8.

Once a plant-optimized DNA sequence has been designed on paper or in silico, actual DNA molecules can be synthesized in the laboratory to correspond in sequence precisely to the designed sequence. Such synthetic DNA molecules can be cloned and otherwise manipulated exactly as if they were derived from natural or native sources. Synthesis of a DNA fragment comprising SEQ ID NO:7 was performed by a commercial supplier (PicoScript, Houston, Tex. USA). The synthetic DNA was then cloned into expression vectors and introduced into cell culture as described in Examples 3 and 4.

Example 3

Expression and Purification of 6X-His Tagged Mcpa for Clinical Studies and Antigen Validation Construction of E. coli expression vector for C-terminal 6X-his-tagged Mcpa. Plasmid DAS28P7B2 was obtained from PicoScript (Houston, Tex.), containing the synthesized plant optimized Mcpa gene between NcoI and SacI restriction sites. The NcoI/SacI fragment was cloned into pET-41a(+) (Novagen, Cat#: 70556-3) and used for expression in E. coli. This vector yielded a truncated protein. Closer examination of the DNA sequence indicated that the Mcpa sequence was not in frame with the pET-41a(+) N-terminal GST, S, and His-tags. To correct the reading frame and to express Mcpa as an N-terminal GST and C-terminal His-tag fusion the following strategy was used.

A DNA fragment was designed and custom synthesized at PicoScript to yield DASPICO19. DASPICO19 contained sequence from the SpeI site of pET-41a(+) to the NcoI site, not including the C-terminal 6X-his tag (region between the N-terminal GST tag and multiple cloning site). This was followed by a small linker region plus the DNA sequence from the EcoRV site to SacI site of DAS28P7B2. This synthetic fragment was used to develop the expression vector for Mcpa, pDAB2448. The cloning steps involved in the construction of Mcpa C-terminal 6Xhis-tag E. coli expression vector, pDAB2448 are illustrated in FIG. 3. A 1.1 kb EcoRV/NcoI fragment from DAS28P7B2 was cloned into DASPICO19, to form pDAB2447. A SpeI/SacI fragment from pDAB2447 was cloned into pET-41a(+) to create pDAB2448.

Expression of C-terminal his-tagged Mcpa. pDAB2448 was introduced into E. coli BL21(DE3) strain and E. coli transformants expressing Mcpa protein were grown overnight to obtain seed. The seed culture was inoculated into 50 ml Luria Broth (LB) containing 50 ug/ml Kanamycin in 250 ml flasks. The culture was grown to an $OD_{600}$ of 0.5 to 1.0 then induced with 1 mM isopropyl-beta-D-thiogalactopyranoside (IPTG) and incubated at 37° C. 2 ml culture samples were taken for protein analysis at 4 h and ~24 h after induction. The cells were then lysed in 200 l of sample buffer and 5 µl of each sample was analyzed on SDS-PAGE gel. Results showed that all of Mcpa protein was in the pellet; this was confirmed by Western blot hybridization. Attempts to obtain soluble expression by modifying induction conditions (i.e. IPTG concentrations, temperature and induction time) did not have any impact on expression of soluble protein.

Figure 4A:
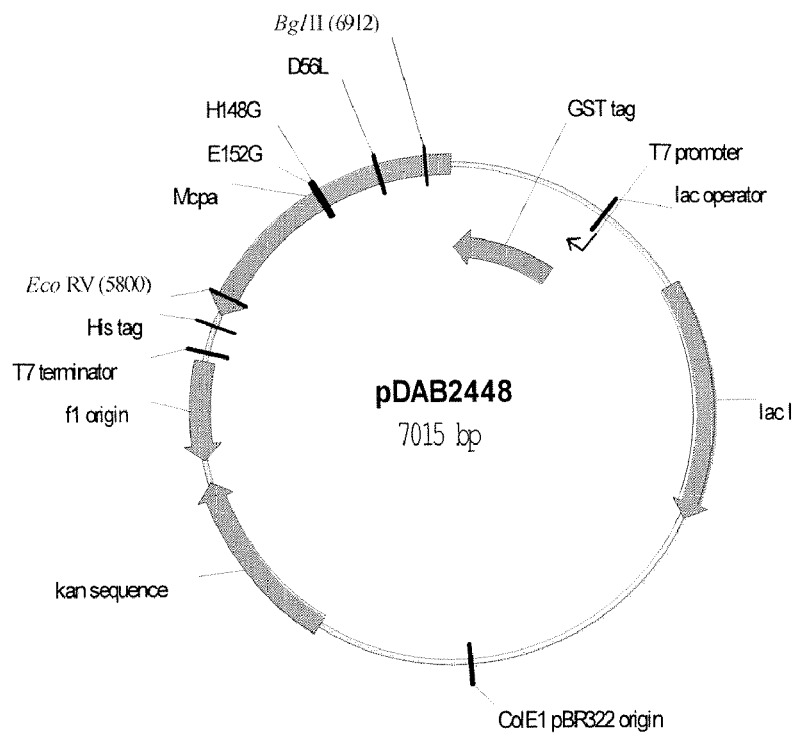
FIG. 4 illustrates cloning steps involved in constructing a vector for expression of N-terminal his-tagged Mcpa in *E. coli*.
Figure 4B:
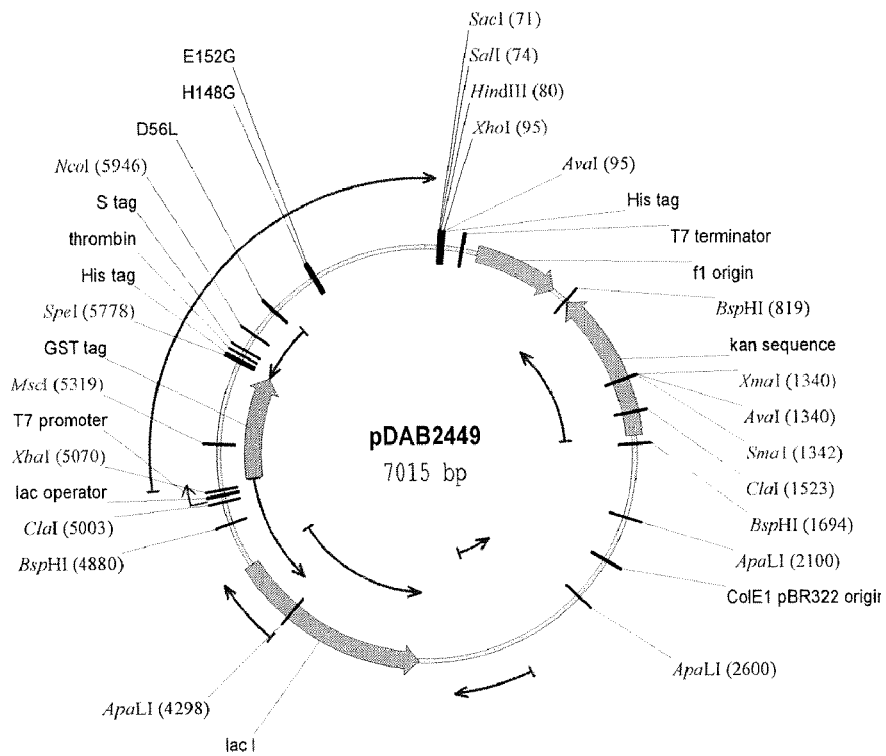

Construction of E. coli expression vector for N-terminal 6X-his-tagged Mcpa. The effect of an N-terminal His-tag on the soluble expression of Mcpa was tested. A new expression vector was made by cloning a BglII/EcoRV fragment of pDAB2448 into the out-of-frame construct previously described. This new expression vector was designated pDAB2449 (FIG. 4).

Expression of N-terminal his-tagged Mcpa. pDAB2449 was transformed into E. coli and expression Mcpa induced using standard conditions as previously described. Results again showed Mcpa as an insoluble protein. Induction conditions were optimized by varying the temperature and IPTG concentrations to obtain soluble expression (variables tested: 20° C. and 37° C.; 20, 100, 250, and 1000 50 µM IPTG; 4 hours and overnight induction). A significant amount of soluble protein was obtained with cultures grown at 20° C. and induced with 250 µM IPTG overnight, or grown at 37° C. and induced with 50 µM IPTG for 4 hours. Cultures were scaled up under both conditions and protein was purified by glutathione sepharose chromatography. Cell pellet from 1 L of culture was lysed in PBS with 0.6 mg/ml lysozyme for 30 min at RT followed by 4×30 sec sonication in a Branson Sonifier. The clarified cell extract was used to purify Mcpa using 10 ml Glutathione Sepharose 4B resin (Amersham). The purified protein was incubated in a buffer containing 25 mM Tris-HCl, pH 8, and 4 mM $CaCl_2$ (New England Biolabs), with varying amounts of enterokinase (EK) for varying incubation times to cleave the GST tag and liberate the Mcpa protein. The reaction was incubated at room temperature with shaking and samples were analyzed by SDS-PAGE. Attempts to cleave the GST tag and retain full-length Mcpa were unsuccessful due to the sensitivity of the N-terminal portion of Mcpa to non-specific EK cleavage. Several attempts to optimize cleavage conditions resulted in truncated alpha toxin. Therefore, the protein was expressed in Pseudomonas fluorescens as a 6X-his-tagged protein with no GST tag.

Construction of Pseudomonas fluorescens expression plasmid for 6X-his tagged Mcpa. The Mcpa gene (SEQ ID NO:9) was PCR amplified from the E. coli expression vector, pDAB2449, which contained full length Mcpa gene as the DNA template, using forward and reverse PCR primers (Integrated DNA Technologies, Skokie, Ill.).

Forward primer: 5' aga gaa cta gta aaa agg aga aat cca tgc atc acc atc acc atc act ccg cgg 3' (SEQ ID NO:14)

Reverse primer: 5' aga gac tcg agc tat cat ttg ata ttg tag gtt gaa ttg c 3' (SEQ ID NO:15)

Figure 5A:
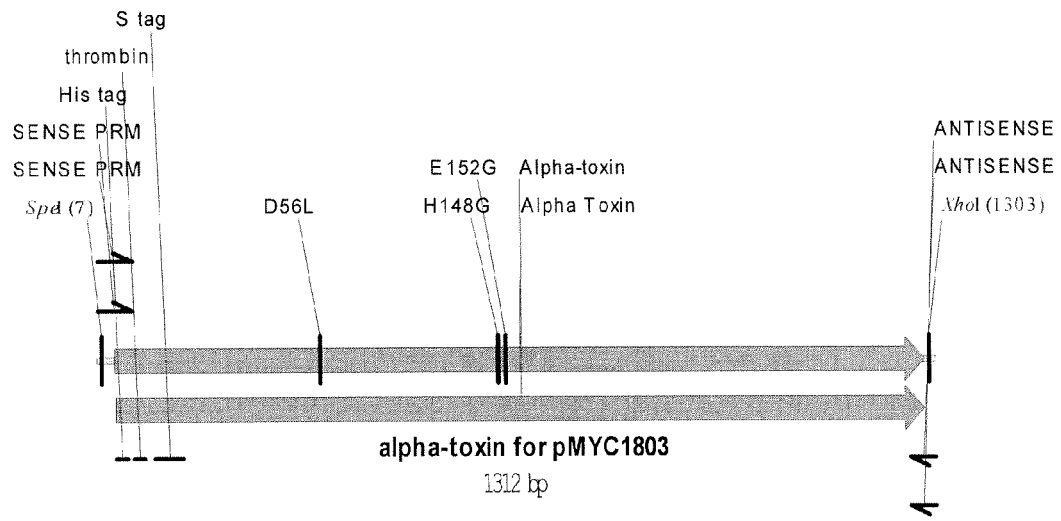
FIG. 5 shows restriction sites of a construct built for expressing his-tagged Mcpa in *Pseudomonas fluorescens*.
Figure 5B:
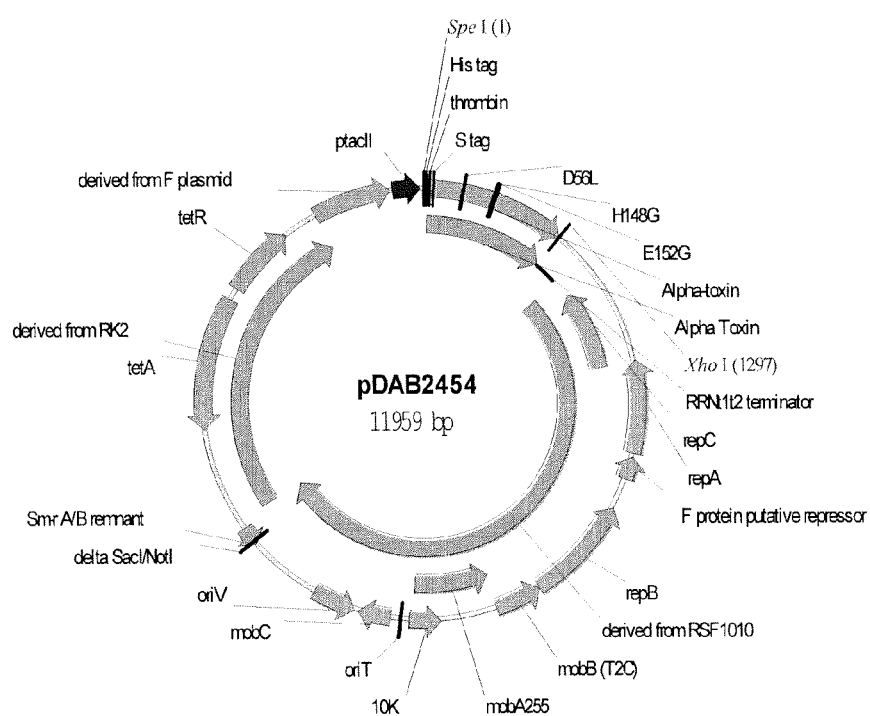

An SpeI restriction site was introduced 5' of the optimized ribosomal binding site using the forward primer and an XhoI site was introduced downstream of the translation stop codon using the reverse primer. This enabled the cloning of the Mcpa gene into a Pf expression vector, resulting in construct pDAB2454 (FIG. 5). Ligation of the synthesized Mcpa N-terminal 6X-his-tagged gene into the SpeI and XhoI sites was accomplished according to Sambrook et al. (1989). Verification of the cloned gene was done with a Beckman Coulter CEQ 2000XL DNA analysis system and analyzed with Sequencher software.

Expression of N-terminal His-tagged Mcpa in *P. fluorescens*. *P. fluorescens* transformation-competent cells were prepared by inoculating 5 ml LB with frozen glycerol stock of *P. fluorescens* MB324 strain, obtained from Dow AgroSciences (DAS) culture collection, and growing overnight at 30° C., shaken at 300 rpm. The following day, 750 µl of overnight culture was inoculated into 50 ml LB contained in a 250 ml flask. Cells were grown to 0.2-0.4 $OD_{600}$. Once proper density was reached, culture sample was chilled on ice for 5-10 minutes, transferred to a 50 ml conical tube, and spun at 7K rpm for five minutes in a Sorvall RC5C floor centrifuge using a GSA rotor. The pelleted cells were washed and resuspended three times with ice cold sterile deionized water before final suspension of cells in 400 µl of sterile water. The ligated DNA was precipitated with ethanol to a 10 µl volume. The 10 µl aliquot of ligated DNA was added to 100 µl of washed cell suspensions in 0.2 cm electroporation cuvettes and electroporated with a BioRad GenePulser at 200 ohms, 25 µF and 2.25 kV at time constants of 4.6 to 4.8. Transformants were allowed to recover for 2 hours at 30° C., 300 rpm and then plated onto LB agar plates containing 30 µg/ml of tetracycline. Plates were incubated at 30° C. for 36-48 hours. Transformants were screened and the Pf expression construct containing full length N-terminal 6X-his-tagged Mcpa. pDAB2454, was verified by restriction enzyme analysis and sequencing of the SpeI and XhoI junctions using Beckman Sequencer and Sequencher software. Glycerol stocks of Pf expressing Mcpa N-terminal 6X his-tag were made and stored at −80° C.

Growth and induction of *P. fluorescens* expressing 6X-his-tagged Mcpa. A 200 µl aliquot of glycerol stock was inoculated into 50 ml LB medium in 250 ml flasks, supplemented with tetracycline to a final concentration of 30 µg/ml. The cultures were incubated in a New Brunswick Innova shaker at 30° C. for ~16 hours at 300 rpm. The overnight seed cultures were then used to inoculate 1 liter of culture medium (see Appendix for Examples 3 and 4) dispensed equally in five 1 liter flasks (2% inoculum and 30 µg/ml of tetracycline). The flasks were incubated in a New Brunswick Innova shaker at 300 rpm and 30° C. for 24 hours after which they were induced with IPTG to a final concentration of 0.3 mM. The cultures were incubated for an additional 48 hours before harvesting.

Purification of 6X-his-tagged Mcpa. After inducing and expressing 1 liter of recombinant Pf culture cells containing the 6X-his-tagged Mcpa protein (SEQ ID NO:10), the cells were pelleted by centrifugation of the culture at 7.5K rpm for 20 minutes and transferred to a 400 ml beadbeater container with 200 ml of 0.1 mm glass beads (BioSpec). The container was filled with phosphate buffer (50 mM sodium phosphate buffer pH 7.5, 0.3 M NaCl), then 2 ml of Sigma protease inhibitor cocktail for His-tagged proteins was added. Cell pellet was lysed by bead beating 8 times for 1 minute each, separated by 1 minute intervals on ice. Following the final bead beating cycle, beads were allowed to settle for 5 minutes on ice before decanting lysed cells into 50 ml Falcon tubes. Lysed cells were then centrifuged at 12K rpm for 15 minutes to separate the lysate from the pellet.

A gravity column containing 20 ml of TALON™ immobilized metal affinity chromatography resin (BD Biosciences) was used to purify the His-tagged Mcpa protein from the lysate. The resin was equilibrated with 20 column volume of 50 mM phosphate buffer, pH 7.5 containing 0.3 M NaCl and the supernatant was carefully passed through the column three times. The flow through sample was collected and placed on ice. The column was then washed again with 20 column volumes of equilibration buffer, followed by 5 column volumes of equilibration buffer containing 10 mM imidazole. The flow through was separately retained. Finally, 5 column volumes of equilibration buffer containing 200 mM imidazole (elution buffer) was used to elute the 6X-his-tagged Mcpa protein from the resin. SDS-PAGE (10% Bis-Tris gel, Invitrogen Corporation) and Western blot analysis were performed using 10 ul of each flow through: no imidazole wash, 10 mM imidazole wash, and 200 mM imidazole elution to confirm the presence of Mcpa in the purified fractions. The purified protein was quantitated by Bradford analysis.

Lyophilization of protein. The proteins were dialyzed into a buffer containing 3 mM Tris-HCl, pH 7.5. Proteins were then quantified using PIERCE Bradford-based protein assay and total protein was calculated. To this, 0.5% trehalose was added and the sample was lyophilized overnight. The weight of the lyophilized protein powder was measured and the percent purity was estimated after subtracting the weight of Tris-HCl buffer, trehalose and residual water. The yield of the final purified protein was >80 mg.

Example 4

Expression and Purification of Nontagged Mcpa for Clinical Studies and Antigen Validation Construction of *Pseudomonas fluorescens* expression plasmid for nontagged Mcpa. The Mcpa gene was amplified out of construct pDAB2454 (Example 3) by a PCR reaction utilizing primers designed with Vector NTI 8 software to exclude the His-tag, S-tag and thrombin sites.

Forward Primer: 5' aga gaa cta gta aaa agg aga aat cca tga gtt ggg atg gaa aga ttg atg gca ctg g3' (SEQ ID NO:16)

Reverse Primer: 5' aga gac tcg agc tat cat ttg ata ttg tag gtt gaa ttg c 3' (SEQ ID NO:15)

For cloning and expression purposes, the primers included a ribosome binding site plus SpeI and XhoI cloning sites. The PCR reaction was carried out using EPICENTRE's FailSafe PCR Protocol and the FailSafe PCR system (cat. # FS99060) with FailSafe PCR 2× PreMix (A, cat. # FSP995A) for 30 cycles of PCR (94° C., 2 min.; 94° C., 1 min.; 52° C., 1 min.; 72° C., 1 min.; 4° C. hold; MJ Research DNA Engine DYAD Peltier Thermal Cycler). The reaction products were purified from a 1% agarose gel following QIAEXII agarose gel extraction (cat. #20051) and digested with SpeI and XhoI. Verification of the PCR product was done with a Beckman Coulter CEQ 200XL DNA analysis system and analyzed with Sequencher software.

The PCR product was ligated into a TOPO® TA (pCR2.1) vector using the Invitrogen TOPO® TA Cloning Kit (cat. # K4500-01) then chemically transformed into *E. coli* competent cells (TOP10F', cat. # K4550-40). Transformants were plated onto LB ampicillin (100 µg/ml) X-galactosidase agar plates and incubated at 37° C. for 24 hours (New Brunswick Scientific Innova 4230 refrigerated incubator shaker). Transformants were screened and the new vector, pDAB3909, was verified by unique restriction enzyme analysis, BamHI and NotI. In addition, the positive clones were further verified by sequencing the SpeI and XhoI junctions, following the Beckman Sequencing Protocol (cat. #608120) with 45 cycles (96° C., 2 min.; 96° C., 20 sec.; 50° C., 20 sec.; 60° C., 4 min.; 4° C., ∞; Gene Amp PCR System 9700) and analyzed with Sequencher 4.1.4 (Gene Codes Corp). DNA gel electrophoresis revealed that positive clones contained the Mcpa gene at approximately 1.2 kb. Glycerol stocks of pDAB3909 were made and stored at −80° C.

Figure 6:
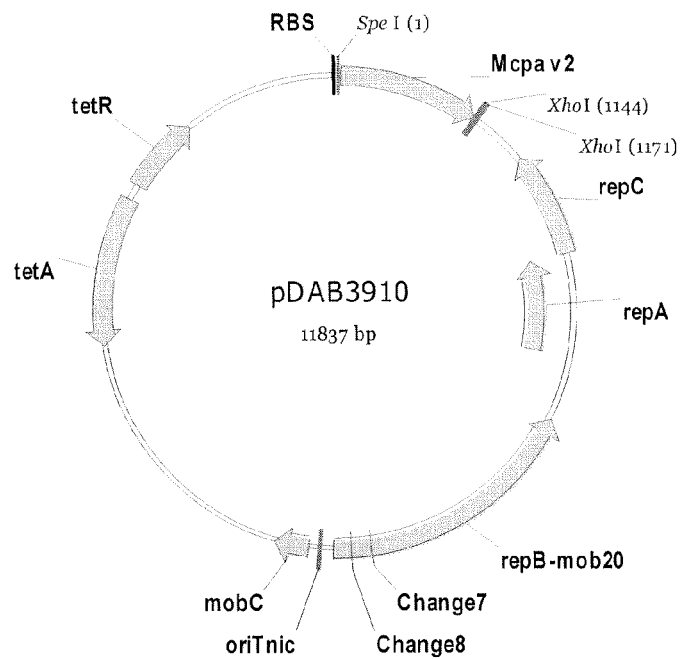
FIG. 6 is a restriction map of a construct built for expressing nontagged Mcpa in *Pseudomonas fluorescens*.

The construction of the nontagged Mcpa expression vector for *P. fluorescens* was completed by cloning the nontagged Mcpa gene (SEQ ID NO:11) from pDAB3909 into the Pf expression plasmid used to obtain pDAB2454. The gene was extracted from pDAB3909 and ligated into the Pf expression plasmid utilizing the SpeI and XhoI sites. The ligation reaction took place overnight in a 16° C. soak (Perkin Elmer Cetus DNA Thermal Cycler). Transformation of the ligated product was done by electroporation using the following protocol. *P. fluorescens* competent cells were prepared by inoculating 5 ml LB with a frozen glycerol stock of *P. fluorescens* MB324 strain and grown overnight at 30° C., shaken at 300 rpm (New Brunswick Scientific Innova 4230 refrigerated incubator shaker). The following day, 750 µl of overnight culture was inoculated into 50 ml LB contained in a 250 ml flask. Cells were grown to 0.2-0.4 $OD_{600}$. Once proper density was reached, culture sample was chilled on ice for 5-10 minutes, transferred to a 50 ml conical tube, and spun at 7K rpm for five minutes in a Sorvall RC5C floor centrifuge using a GSA rotor. The pelleted cells were washed and resuspended three times with ice cold sterile deionized water before final suspension of cells in 400 µl of sterile water. The ligated DNA was precipitated with ethanol to a 10 µl volume. The 10 µl aliquot of ligated DNA was added to 100 µl of washed cell suspensions in 0.2 cm electroporation cuvettes and electroporated with a BioRad GenePulser at 200 ohms, 25 µF and 2.25 kV at time constants of 4.6 to 4.8. Transformants were allowed to recover for 2 hours at 30° C., 300 rpm and then plated onto LB agar plates containing 30 µg/ml of tetracycline. Plates were incubated at 30° C. for 36-48 hours. Transformants were then screened and the final construct, pDAB3910, was verified by restriction enzyme analysis. Glycerol stocks of pDAB3910 (FIG. 6) were made and stored at −80° C.

Growth and induction of *P. fluorescens* expressing nontagged Mcpa. Frozen glycerol stocks of *Pseudomonas fluorescens* containing plasmid, pDAB3910, were used for nontagged Mcpa protein expression (SEQ ID NO:12). A 200 µl aliquot of glycerol stock was inoculated into 50 ml LB medium in 250 ml flasks, supplemented with tetracycline to a final concentration of 30 µg/ml. The cultures were incubated in a New Brunswick Innova shaker at 30° C. for ~16 hours at 300 rpm. The overnight seed cultures were then used to inoculate 1 liter of culture medium (see Appendix for Examples 3 and 4) dispensed equally in five 1 liter flasks (2% inoculum and 30 µg/ml of tetracycline). The flasks were incubated in a New Brunswick Innova shaker at 300 rpm and 30° C. for 24 hours after which they were induced with IPTG to a final concentration of 0.3 mM. The cultures were incubated for an additional 48 hours before harvesting.

After 48 hours, the cultures were poured into sterile 500 ml centrifuge bottles and centrifuged in a Sorvall RC5C centrifuge at 8165×g for 15 minutes. The supernatants were discarded and the pellets were stored at −80° C. Each culture was subsequently screened and the final construct, pDAB3910, was verified by restriction enzyme analysis and by sequencing the SpeI and XhoI junctions utilizing the Beckman Sequencing Protocol for 45 cycles (96° C., 2 min.; 96° C., 20 sec.; 50° C., 20 sec.; 60° C., 4 min.; 4° C. hold; Gene Amp PCR System 9700) and analyzed with. Sequencher 4.1.4 (Gene Codes Corp). A 2 liter scale-up and harvest of Pf cells transformed with the nontagged Mcpa gene was done following the procedures described above.

Purification of nontagged Mcpa protein. A 24 g aliquot of cell paste was resuspended in 200 ml of Lysis Buffer (50 mM Tris pH 8.0, 5% (v/v) glycerol, 20 mM EDTA, 0.5% (v/v) Triton X-100, 1 mM DTT) and 1X Protease inhibitor cocktail (Sigma cat. # P8465) and lysed by bead beating with 0.1 mm glass beads in a 450 ml disruption chamber (BioSpec). The cells were processed 7 times at one-minute intervals separated by 1-minute rest periods on ice to prevent overheating. Additionally, the chamber was cooled by ice. The lysate was placed in 250 ml centrifuge bottles and spun at 14,000×g in a SLC-1500 rotor for 20 minutes. The supernatant was filtered three times, (0.85 µm, 0.45 µm, and 0.22 µm). The pellet was discarded.

Figure 7:
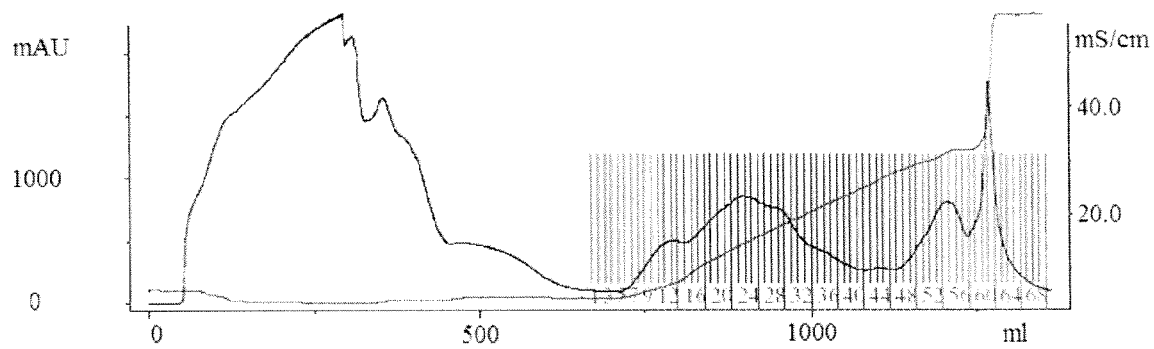
FIG. 7 shows recovery of nontagged Mcpa from *P. fluorescens* culture using purification by anion-exchange chromatography and SDS-PAGE of eluted fractions.

The clarified sample was purified by anion-exchange chromatography by loading onto a Q Sepharose XK 26/11 column equilibrated with Buffer A (50 mM Tris pH 8.0, 5% (v/v) glycerol, 20 mM EDTA, 0.5% (v/v) Triton X-100, 1 mM DTT) at 5 ml/min. The Mcpa protein was eluted with 10 column volume (CV) linear gradient to 50% Buffer B (Buffer A+1 M NaCl) for 100 minutes and then 100% Buffer B. 10 ml fractions were collected and the elution profile was obtained (FIG. 7).

SDS-PAGE analysis of the eluted fractions indicated the presence of Mcpa protein at approximately 42 kDa. A close-up was prepared of the chromatogram overlayed with a picture of SDS-PAGE analysis of the fractions taken. The location of the nontagged Mcpa protein in the SDS-PAGE was noted.

SDS-PAGE fractionated proteins were transferred to a nitrocellulose membrane in Tris-glycine buffer with 20% methanol at 100 volts for 60 minutes for Western blot analysis. The blot was briefly incubated in PBS-Tween (Pierce, Rockford, Ill.), then blocked in 5% v/v milk and 0.5% Tween 20 blocking buffer dissolved in PBS for 60 minutes at room temperature. Rabbit Anti-CPA (Dow AgroSciences, Lot # DAS1041-156-2) was used as the primary antibody. The antibody was diluted to 1 μg/ml in a fresh aliquot of blocking buffer and incubated with the blot for 60 minutes at room temperature. The blot was washed with PBS 2 times for 15 minutes at room temperature. Goat Anti-Rabbit IgG (KPL Cat No. 075-1506) antibody with an alkaline phosphate conjugate was used to detect the primary antibody. The antibody was diluted 1/1000 in a fresh aliquot of blocking buffer and incubated with the blot for 60 minutes at room temperature. The blot was washed in PBS 3 times for 10 minutes at room temperature. The blot was developed with NBT/BCIP (Pierce, Rockford, Ill. cat. #34042) and washed with distilled water and air-dried.

An SDS-PAGE and a Western blot were prepared from pooled fractions 56-70, as compared to purified tagged Mcpa (Example 3) and a negative control (lysate from cells transformed with empty vector). The gel indicated 90% nontagged Mcpa sample purity. In the Western Blot, some occurrences of aggregation and degradation of the Mcpa band were observed. In addition, cross reactivity was noted in the negative control.

Matrix-assisted laser desorption/ionisation-time of flight (MALDI-TOF) mass spectrometry and N-terminal sequencing of nontagged Mcpa were also used to verify the identity of the purified protein. The N-terminal sequence of the sample (S W D G K I D G T G) matched the expected Mcpa sequence from residues #2 to 11 at the N-terminus. After trypsin digestion of the sample, peptides detected by MALDI-TOF were compared with the expected peptide mass fingerprint (PMF) of Mcpa using PAWS software (Genomic Solutions, Inc.). A total of 18 peptides from nontagged Mcpa were identified, yielding a PMF coverage of 56%. This analysis strongly indicated that the PMF of the sample matched the theoretical sequence of nontagged Mcpa.

The cleanest fractions (Fractions 56-70) were pooled and concentrated to approximately 35 ml with Millipore 10K-MWCO spin concentrators (used according to the manufacturer's directions). The concentrate was injected into Snake Skin Slide-A-Lyzer dialysis cassettes (3.5-k MWCO, cat. # GD96524) and dialyzed overnight against 2 liters of 1×PBS pH 8.0 at 4° C. The dialyzed sample was dispensed into two ~25 ml aliquots, shell frozen in pre-tared 50 ml conical Falcon tubes and lyophilized for 2 days (Virtis Freezemobile 25 EL). Lyophilization yielded 1.13 g of powder which was stored at 4° C. Total protein concentration was determined (Bradford assay) and purity calculated at 2.2% by weight, yielding approximately 25 mg nontagged Mcpa.

In summary, a 25 mg sample of nontagged Mcpa was purified from 400 ml of Pf culture via anion-exchange chromatography. The purification scheme can be further optimized. Additionally, dialysis against 3 mM Tris pH 8.0 with 0.5% trehalose, rather than 1×PBS buffer is recommended for long term stability of the protein. The generated nontagged Mcpa was used as a test antigen.

Appendix for Examples 3 and 4

*Pseudomonas fluorescens* Seed Flask Medium

LB medium (Miller or Lennox is fine)

Aliquot 50 or 100 ml medium into 250 ml flask.

Close with foam plug and cover.

Autoclave 20 min. at 121° C.

Example 5

Toxicity Testing of Purified Recombinant Cpa Proteins

Two in vitro assays were developed, each for detection of a characteristic activity of native Cp alpha toxin, Red Blood Cell (RBC) hemolysis or lecithinase. In the hemolysis assay, red blood cells (RBCs) were incubated with putative nontoxic cpa and observed for hemolytic effects as compared to positive and negative controls. The assay was useful for determining the approximate activity or concentration of phospholipase C (PLC) in experimental samples, based on a standard containing a known amount of PLC units.

Lecithin (L-α phosphatidylcholine) is the most abundant phosphoglyceride, a phospholipid which serves as a major structural component of cell membranes. When alpha toxin is secreted from Cp, it natively binds to host cell membranes, cleaves lecithin, and triggers a cascade of events which results in decreased oxygen to the bacterially-infected site and the proliferation of Cp. A second assay was developed and used to measure lecithinase activity of experimental samples and thus determine the approximate activity or concentration of PLC by comparison to a standard (Logan, 1991). Lecithinase activity was detected and quantified in vitro by incubation of cpa recombinant proteins with a lecithinase solution. Increased turbidity, as measured by spectrophotometry, indicated cleavage activity. Both assays were instrumental in demonstrating effective design of antigens in removing or reducing hemolytic and lecthinase toxic activities, prior to initiation of animal studies.

RBC Lysis Assay for Detection of *Clostridium perfringens* Alpha-Toxin Activity

Preparation of PLC standard. Lyophilized PLC standard (Sigma P-4039, 500 units, Lot no. 014K86152) was opened in a clean biosafety cabinet. The contents of the PLC vial were rehydrated with sterile DPBS (Cellgro Cat No. 21-031-CV) to a final concentration of 106 PLC units/mL, for use as a stock solution. The stock solution was stored in 50 μL aliquots in cryovials at −80° C. until used.

Calcium borate buffer. Calcium borate buffer was used to dilute all samples tested. The buffer was prepared using the following procedure: 200 mM Boric acid (Sigma) and 1.3 mM Calcium chloride (Sigma) dissolved in 500 mL RO/DI water. pH to 7.6 with 100 mM Sodium Tetraborate (Borax) (19 g/500 mL RO/DI water); volume adjusted to 1 L. The buffer was stored at room temperature, with a one year expiration date.

1% (v/v) Red Blood Cell solution. A solution of 1% (v/v) chicken RBCs (cRBC) (Colorado Serum Company: Catalog No. CS 1151) was prepared using DPBS for washing and dilution as follows:

1. Transfer 5 mL cRBCs in Alsevers solution into a 15 mL conical tube.
2. Centrifuge at 250×g for 10 minutes to pellet cRBCs.
3. Aspirate supernatant and white blood cells from the top of the pellet.
4. Resuspend pellet in 10 mL saline.
5. Pellet cells at 250×g for 10 minutes.
6. Repeat steps 3-5 two additional times, or until the supernatant is clear. (If the supernatant remains red after the third wash in saline, stock cRBCs are too old and should be destroyed. Note that the cRBCs in Alsevers solution are stable for approximately 2 weeks at 2-7° C.)
7. After the final wash in saline, aspirate the supernatant and save the packed cRBC pellet.
8. Dilute the cRBCs to 1% (v/v) in DPBS buffer. Note that approximately 5 mL of the 1% cRBC solution is required per plate on test.
9. Determine the Absorbance at 540 nm of the lysed blood cells in the 1% solution. The acceptable range is 0.4-0.5 $A_{540}$.
   - i. Transfer 400 μL of the 1% (v/v) cRBC solution to a small tube and add 1.6 mL of RO/DI water.
   - ii. Vortex on highest setting for 20 seconds to lyse cells.
   - iii. Blank the spectrophotometer with 400 μL DPBS buffer in 1.6 mL water at 540 nm.
   - iv. Transfer the lysed cRBC solution to a cuvette and read absorbance at 540 nm.
   - v. If the absorbance at 540 nm is 0.4 to 0.5 the 1% solution is acceptable for use in the assay. If the absorbance at 540 nm is <0.4 or >0.5 the 1% solution must be adjusted by adding DPBS buffer to decrease the absorbance to within the range or adding additional cRBCs from the cell pellet to increase the absorbance. If the 1% solution is adjusted due to absorbance at 540 nm that is outside the limits, the adjusted cRBC solution must be lysed and the new $A_{540}$ determined. Alternatively, a new 1% cRBC solution can be prepared and reassayed if the initial 1% solution is out of range.

Assay procedure. The wells of a 96 well U-bottom plate (Falcon Catalog No. 35-3918) were loaded with 50 μL of Calcium Borate Buffer. Sample or PLC stock solution (50 μL) was then added to the first well of a row or column. The sample or control was mixed and serially diluted to subsequent wells by transferring 50 μL until the desired end dilution was achieved. The remaining 50 μL was removed from the last dilution well and discarded so that each well contained 50 μL of sample or control. Fifty μL of 1% RBCs solution was then added to all wells and the plate was mixed on a plate shaker for 30 seconds. The plate was incubated at 37° C.±2° C. for one hour. A plate reader was used to determine the absorbance of each well at 620 nm. An image of the plate was also captured using a Syngene GeneGenius Bio Imaging System imager.

RBC lysis data was analyzed using the $A_{620}$ values as well as a visual qualitative analysis of the wells on the plate. Complete lysis of RBCs was indicated by a low $A_{620}$ value and by a cloudy well with no cells collected at the bottom of the plate. Partial lysis produces a cloudy well with a small "button" of RBC at the bottom of the plate that is smaller than the control wells. No lysis was indicated by a complete collection of all RBCs at the bottom of the well and clear buffer above the collection of RBCs. Lysis of RBCs was an in vitro indication of biological activity of the samples and/or controls.

Samples were tested alongside standards containing known concentrations of PLC, allowing for determination of the concentration of PLC in a sample by comparison to a standard curve. The negative controls included buffer without sample or standard and 1% RBCs without buffer. Validity of the assay was dependent on the negative controls indicating no lysis activity at any dilution.

Figure 8:
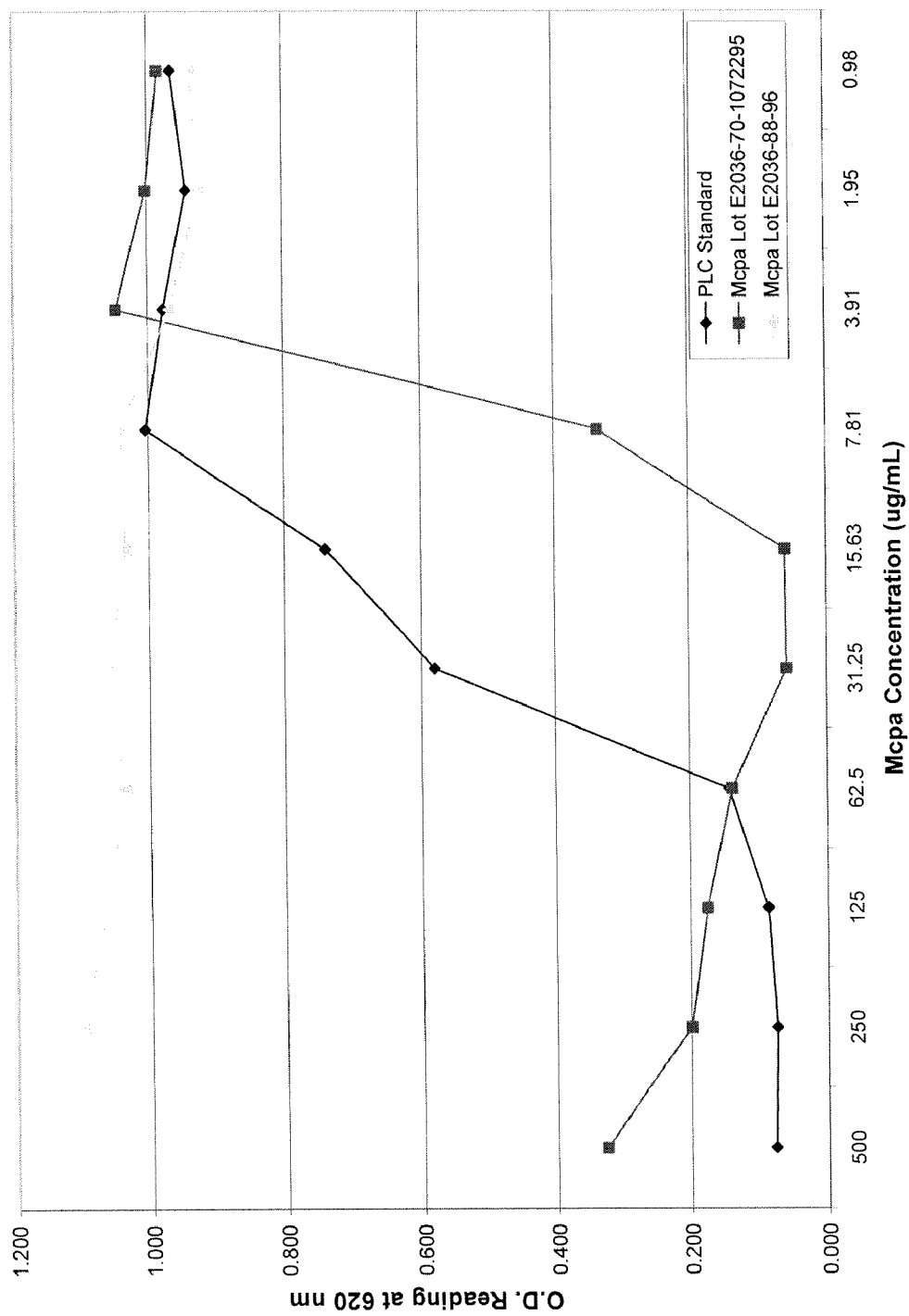
FIG. 8 demonstrates loss of hemolytic activity in purified nontagged Mcpa; also shown is presence of hemolysis due to residual detergent in the sample.

Testing purified Mcpa recombinant proteins from bacterial sources. The mutant cpa (Mcpa) was expressed in and purified from *Pseudomonas fluorescens* (Pf) for use as a reference antigen (Examples 3 and 4). The 6X-his-tagged version of Mcpa (SEQ ID NO:10. Lot no. DAS F1041-188-2, Example 3) was evaluated in the RBC lysis assay and no hemolytic activity was detected in the maximum concentration tested (500 μg/mL, Table 4). A nontagged version (NHT Mcpa, SEQ ID NO:12, Example 4) was also generated in Pf and purified (Lot No. E2036-70-1072295). However, this protein was found to lyse RBCs at concentrations as low as 7.81 μg/mL Since the His tag was not present for purification, an alternate method had been used including Triton X-100 detergent (0.5% v/v) in the purification buffer. It was speculated that residual Triton X-100 in the preparation might be responsible for the hemolysis. Another lot of NHT Mcpa (Lot No. E2036-88-96) was produced with more diligent removal of the detergent, and tested in the RBC lysis assay. Results indicated that when Triton X-100 was more completely removed, RBC lysis activity was not detected (FIG. 8). Lot E2036-88-96 of NHT Mcpa in the absence of residual Triton X-100 did not lyse chicken RBCs up to a concentration of 500 μg/mL. The endpoints of PLC activity in all three Mcpa lots are summarized in Table 4.

Lecithinase Assay for Detection of *Clostridium perfringens* Alpha-Toxin Activity.

Egg Yolk Emulsion. Egg yolk emulsion (Oxoid SR0047C) was used as the lecithin source for the in vitro assay. Emulsion was centrifuged at 10,000×g for 20 minutes. Supernatant was collected and diluted 1:8 with 0.9% calcium borate buffer (0.002M CaCl, 0.2 M $H_3BO_3$, pH 7.6)

Assay procedure. Fifty μL aliquots of test samples and phospholipase C (PLC) positive control (previously described, Sigma P-4039) were added to wells of a 96 well plate. Each sample was serially diluted in calcium borate buffer, maintaining a total volume of 50 μL per well. Fifty μL of egg yolk emulsion was then added per well. The plate was placed on a shaker for 30 seconds and read at 620 nm for a baseline reading. The plate was incubated at 37° C. for 1 hour and a final plate read at 620 nm was done. The increase in $A_{620}$ values at 1 hour over the baseline reading was calculated. PLC activity was interpreted as a 50% or greater increase in well turbidity. Calculations were performed using the following equation:

% increase in turbidity=[100×(1 hour reading/0 hour reading)]−100

Figure 9:
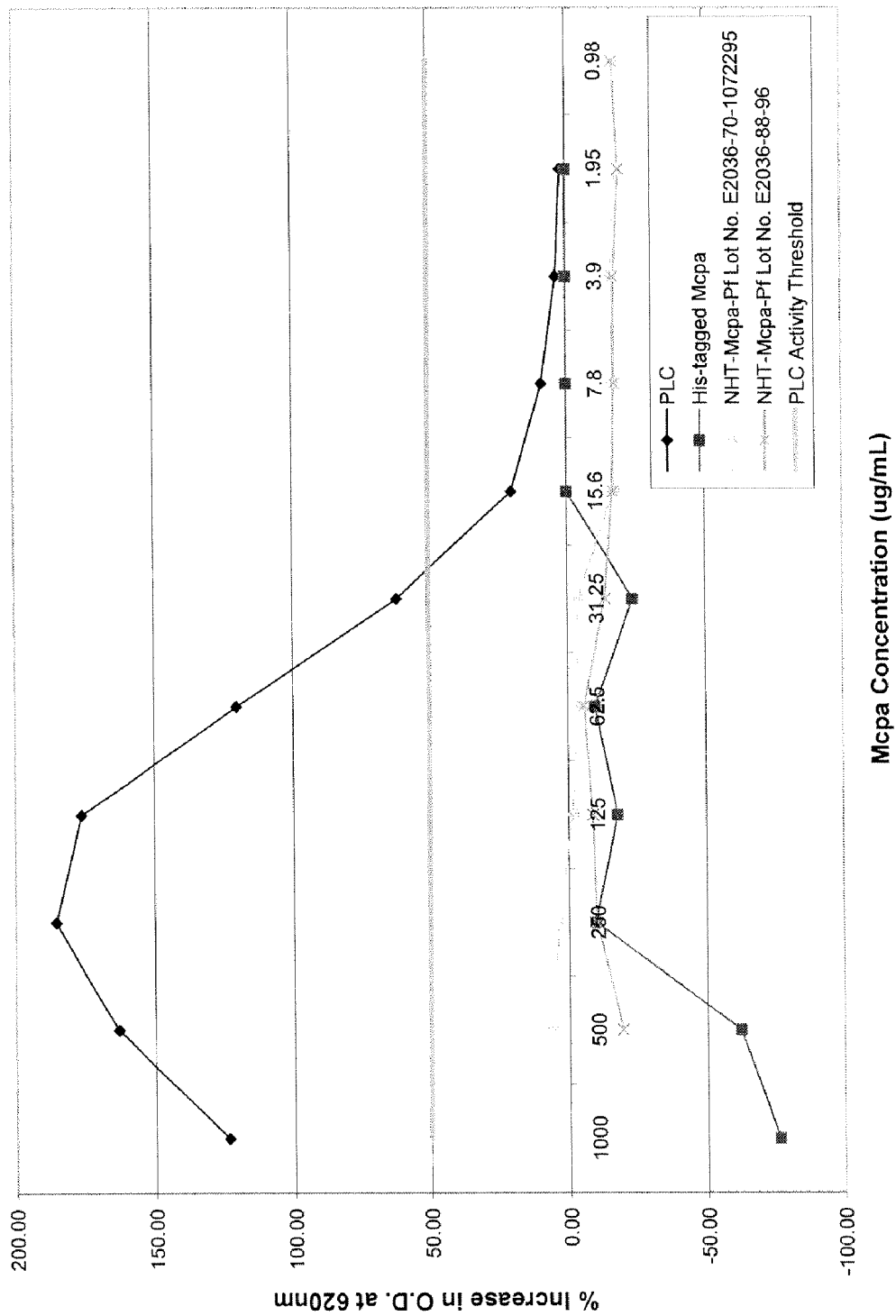
FIG. 9 shows absence of lecithinase activity in purified samples of Mcpa.

Testing purified Mcpa recombinant proteins from bacterial sources. His-tagged Mcpa and nontagged Mcpa (NHT Mcpa) from Examples 3 and 4, expressed in and purified from *P. fluorescens* were evaluated for lecithinase activity. His-tagged Mcpa protein demonstrated no PLC activity in the lecithinase assay when tested up to a concentration of 1000 μg/mL. The NHT Mcpa antigens did not exhibit lecithinas activity either, up to the maximum concentration tested, 500 μg/mL (FIG. 9).

Lecithinase and hemolysis evaluation of the Mcpa purified antigens demonstrated these α toxin activities were greatly reduced or eliminated through design of novel point mutations of the full-length protein.

Example 6

Subcutaneous Vaccination with Recombinant Mutant Alpha Toxin for Protection of Chicks Against Necrotic Enteritis Vaccine preparation. Lyophilized samples of purified Mcpa and NHT Mcpa as described in Examples 3 and 4 (Lot numbers DASF1197-08-03, Mcpa (Pf); and DASE2036-88-96, nontagged Mcpa (Pf)) were stored at −20° C. before use. For vaccine formulation, the antigens were rehydrated with sterile water and 1 mM EDTA was added. Mcpa and NHT Mcpa were formulated with lecithin acrylic polymer plus Quil A cholesterol (LAP/QAC) with a Quil A:cholesterol ratio of 1:1 or 4:1 by weight, as indicated in the study design (Table 5).

Study procedure. Cornish Rock cross broilers were received on day of hatch (Day 0) from McMurray Hatchery, Webster City, Iowa and housed in pegboard brooders on shavings with continuous lighting. Low protein-Fish Meal Starter (LP-FM Starter, Lot Number 092505) supplemented with zinc to 400 ppm was provided (APPENDIX for Example 6) in the amount of approximately 750 g per day per treatment group; chicks had free access to water.

Birds were vaccinated on Days 5 and 15 as indicated in the study design. Vaccines were formulated on the day of injection and administered subcutaneously at the back of the neck.

On Day 8, chicks were switched to High Protein-Fish Meal Grower (HP-FM Grower, Lot Number 100405) supplemented with zinc to 400 ppm for the duration of the study (APPENDIX for Example 6).

Feed was withdrawn on Day 24 for approximately 20 hours. Challenge followed, twice per day for 4 days, with Cp strain JGS 4143 in feed (100 g feed per 125 mL culture). The Cp component of the mixture was prepared as follows: Cp cultures stored at −80° C. were inoculated into 100 mL volumes of fluid thioglycollate media (FTG) and incubated at 37±2° C. for 18 hours. A 5% inoculum was transferred into 100 mL volumes of cooked meat media (CMM), followed by incubation at 37° C.±2° C. for 18 hours. Finally, 1 L volumes of FTG inoculated with 5% of the CMM culture were incubated at 37° C.±2° C. for 18 hours prior to mixing with feed.

Birds were observed for signs of NE (depression, inappetance, malaise, diarrhea, ruffled feathers) and those exhibiting severe signs were euthanized for necropsy and lesion scoring. Surviving birds were necropsied and lesion scores recorded on Day 29.

Scoring System for Necropsy

0: no gross lesions

1+: small intestine dilated and thin-walled or friable; contains yellow/brown, watery, foul smelling content; thickened mucosal layer separated from the muscularis mucosa; erosion or sloughing of villus tips, accumulation of necrotic debris, fibrin, and bacteria 2+: edema and hyperemia; focal necrosis or ulceration of small intestine; moderate erosion of villus tips 3+: large patches of necrosis and ulceration; hemorrhage; mucosal sloughing\

4+: necrosis of entire gut lining, including complete sloughing in discrete areas; pseudomembrane often present; villus erosion; typical of field cases Data analysis. Lesion scores for all treatments were first analyzed together as a simple list of treatments with no structure. Next, a subset of treatments T4-T7 was further analyzed as a Factorial with two levels. The first level compared Tagged vs. Non-tagged Mcpa and the second level compared the LAP/QAC ratios 1:1 to 4:1. The lesion score data was analyzed as an ordered categorical measure and the analysis was a Contingency analysis. If this analysis was significant, the individual treatments were then compared using simple contingency analyses of every possible pair of treatments. All analyses were performed using the JMP statistical package.

Figure 10:
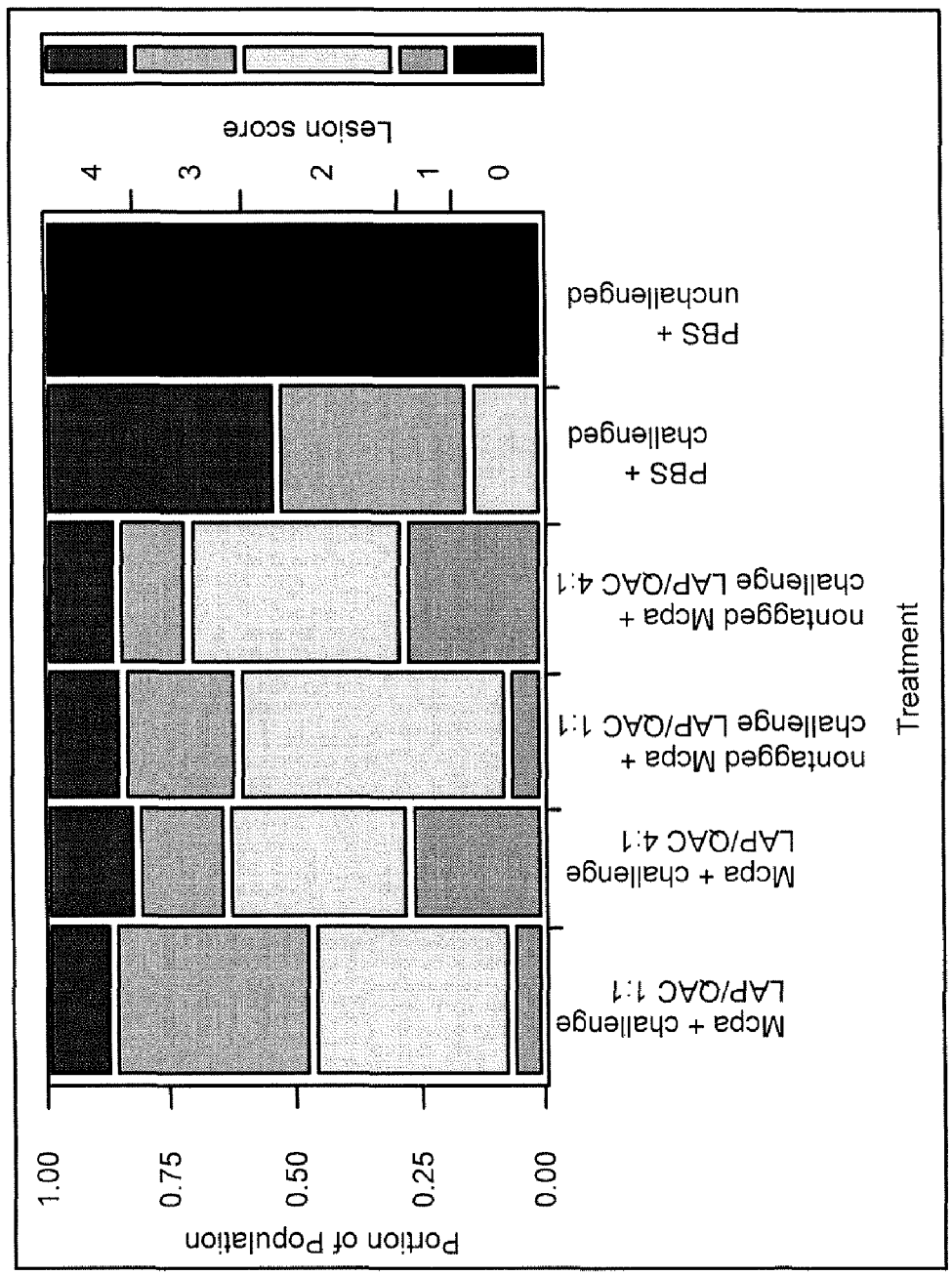
FIG. 10 is a mosaic plot of lesion scores per treatment group, resulting from a clinical study to evaluate the utility of formulated Mcpa as a subcutaneous vaccine for protection against NE.

Lesion Scores. Frequency of lesion scores per treatment group is summarized in Table 6. Analysis showed significant differences between treatments (p=0.001). A mosaic plot (FIG. 10) illustrates frequency of lesion scores per group, with nonscorable birds removed from the data set. Analysis revealed all challenged treatments were significantly different from the unchallenged control and that treatment T4 (Mcpa(Pf)[LAP/QAC 4:1]), and T6 (nontagged Mcpa(Pf) [LAP/QAC 4:1]) were significantly different from the non-vaccinated, challenged controls (p=0.0239, and p=0.0116, respectively, Table 7). These data strongly indicate the Pf-derived recombinant mutant alpha toxins, either tagged or nontagged, with the LAP/QAC 4:1 adjuvant were effective in reducing the severity of Necrotic Enteritis lesions in chicks when administered as a subcutaneous vaccine.

APPENDIX for Example 6
Composition of Feed

| Component | % of Composition |
|---|---|
| Low Protein - Fish Meal Starter (LP-FM) | |
| Wheat (Feedmill) | 85.00 |
| Soybean Meal (Bulk) | 3.00 |
| Fish Meal | 6.00 |
| Liquid Fat (Bulk) | 2.00 |
| Di-Cal (Co-Phos) | 0.74 |
| Limestone | 0.90 |
| Rock Salt | 0.36 |
| Trace Minerals | 0.10 |
| Vit A-D-E | 0.10 |
| Methionine | 0.10 |
| Dyna K KCl | 0.80 |
| Lysine | 0.90 |
| Total | 100.00 |
| High Protein-Fish Meal Grower (HP-FM Grower) | |
| Wheat (Feedmill) | 33.5 |
| Soybean Meal (Bulk) | 14.7 |
| Fish Meal | 50.0 |
| Liquid Fat (Bulk) | 1.25 |
| Limestone | 1.75 |
| Rock Salt | 0.225 |
| Trace Minerals | 0.075 |
| Vit A-D-E | 0.075 |
| Total | 100 |

Zinc supplemented to approximately 400 ppm

TABLE 1

Variations in chicken alpha-toxins compared to Strain 13 (human isolate)

| AA No. | Str13* | Type I* | Type II* | Type III* | Type IV* | Type V* | Type VI |
|---|---|---|---|---|---|---|---|
| 13 | T | A | A | T | A | A | T |
| 15 | A | A | A | V | A | A | A |
| 22 | A | A | A | V | A | A | A |
| 47 | V | V | V | V | V | V | I |
| 54 | L | L | L | M | M | L | L |
| 71 | E | E | E | D | E | E | Q |
| 149 | L | L | L | I | L | L | L |
| 202 | D | D | D | D | D | A | A |
| 205 | A | A | A | A | A | T | A |
| 373 | I | I | V | V | I | I | V |

*Sheedy et al. (2004)

TABLE 2

Synonymous codon representation in coding regions of 32,630 *Oryza saliva* (rice) genes (Columns C and I), and 1268 *Nicotiana tabacum* (tobacco) genes (Columns D and J). Values for a balanced-biased codon representation set for a plant-optimized synthetic gene design are in Columns F and L.

| A<br>Amino<br>Acid | B<br>Codon | C<br>Rice<br>% | D<br>Tobacco<br>% | E<br>Rice-<br>Tobacco<br>Average | F<br>Weighted<br>Average | G<br>Amino<br>Acid | H<br>Codon | I<br>Rice<br>% | J<br>Tobacco<br>% | K<br>Rice-<br>Tobacco<br>Average | L<br>Weighted<br>Average |
|---|---|---|---|---|---|---|---|---|---|---|---|
| ALA (A) | GCA | 18.8 | 31.0 | 24.9 | 30.4 | LEU (L) | CTA | 9.0 | 10.5 | NA | DNU |
|  | GCC | 32.3 | 17.3 | 24.8 | 30.2 |  | CTC | 27.3 | 13.0 | 20.2 | 25.6 |
|  | GCG | 27.9 | 8.1 | NA | DNU |  | CTG | 22.6 | 11.2 | 16.9 | 21.4 |
|  | GCT | 21.0 | 43.6 | 32.3 | 39.4 |  | CTT | 16.8 | 25.9 | 21.3 | 27.0 |
| ARG (R) | AGA | 15.0 | 31.7 | 23.3 | 32.8 |  | TTA | 7.3 | 15.3 | NA | DNU |
|  | AGG | 21.8 | 24.6 | 23.2 | 32.6 |  | TTG | 16.9 | 24.0 | 20.5 | 26.0 |
|  | CGA | 10.4 | 11.9 | 11.2 | 15.7 | LYS (K) | AAA | 34.3 | 50.0 | 42.1 | 42.1 |
|  | CGC | 22.5 | 8.1 | NA | DNU |  | AAG | 65.7 | 50.0 | 57.9 | 57.9 |

TABLE 2-continued

Synonymous codon representation in coding regions of 32,630 *Oryza saliva* (rice) genes (Columns C and I), and 1268 *Nicotiana tabacum* (tobacco) genes (Columns D and J). Values for a balanced-biased codon representation set for a plant-optimized synthetic gene design are in Columns F and L.

| A Amino Acid | B Codon | C Rice % | D Tobacco % | E Rice-Tobacco Average | F Weighted Average | G Amino Acid | H Codon | I Rice % | J Tobacco % | K Rice-Tobacco Average | L Weighted Average |
|---|---|---|---|---|---|---|---|---|---|---|---|
| | CGG | 19.4 | 7.7 | NA | DNU | MET (M) | ATG | 100.0 | 100.0 | 100.0 | 100.0 |
| | CGT | 11.0 | 16.0 | 13.5 | 19.0 | PHE (F) | TTC | 61.6 | 41.9 | 51.8 | 51.8 |
| ASN (N) | AAC | 54.7 | 39.4 | 47.1 | 47.1 | | TTT | 38.4 | 58.1 | 48.2 | 48.2 |
| | AAT | 45.3 | 60.6 | 52.9 | 52.9 | PRO (P) | CCA | 24.8 | 38.9 | 31.8 | 31.8 |
| ASP (D) | GAC | 52.2 | 31.1 | 41.6 | 41.6 | | CCC | 21.1 | 13.6 | 17.3 | 17.3 |
| | GAT | 47.8 | 68.9 | 58.4 | 58.4 | | CCG | 30.5 | 10.0 | 20.3 | 20.3 |
| CYS (C) | TGC | 65.2 | 42.6 | 53.9 | 53.9 | | CCT | 23.7 | 37.5 | 30.6 | 30.6 |
| | TGT | 34.8 | 57.4 | 46.1 | 46.1 | SER (S) | AGC | 20.3 | 12.5 | 16.4 | 18.5 |
| END | TAA | 24.7 | 42.6 | 33.7 | | | AGT | 11.6 | 17.3 | 14.5 | 16.3 |
| | TAG | 31.8 | 19.6 | 25.7 | | | TCA | 15.5 | 22.6 | 19.0 | 21.5 |
| | TGA | 43.5 | 37.8 | 40.6 | | | TCC | 20.5 | 14.1 | 17.3 | 19.6 |
| GLN (Q) | CAA | 41.0 | 58.9 | 50.0 | 50.0 | | TCG | 15.8 | 7.2 | NA | DNU |
| | CAG | 59.0 | 41.1 | 50.0 | 50.0 | | TCT | 16.4 | 26.2 | 21.3 | 24.1 |
| GLU (E) | GAA | 36.9 | 55.7 | 46.3 | 46.3 | THR (T) | ACA | 23.7 | 32.7 | 28.2 | 33.7 |
| | GAG | 63.1 | 44.3 | 53.7 | 53.7 | | ACC | 30.5 | 19.1 | 24.8 | 29.6 |
| GLY (G) | GGA | 21.4 | 34.6 | 28.0 | 28.0 | | ACG | 23.6 | 8.8 | DNU | DNU |
| | GGC | 37.0 | 16.2 | 26.6 | 26.6 | | ACT | 22.3 | 39.4 | 30.8 | 36.8 |
| | GGG | 22.3 | 15.4 | 18.9 | 18.9 | TRP (W) | TGG | 100.0 | 100.0 | 100.0 | 100.0 |
| | GGT | 19.3 | 33.7 | 26.5 | 26.5 | TYR (Y) | TAC | 58.8 | 41.4 | 50.1 | 50.1 |
| HIS (H) | CAC | 54.5 | 38.3 | 46.4 | 46.4 | | TAT | 41.2 | 58.6 | 49.9 | 49.9 |
| | CAT | 45.5 | 61.7 | 53.6 | 53.6 | VAL (V) | GTA | 10.7 | 18.3 | NA | DNU |
| ILE (I) | ATA | 20.8 | 25.8 | 23.3 | 23.3 | | GTC | 29.8 | 17.0 | 23.4 | 27.4 |
| | ATC | 45.2 | 24.6 | 34.9 | 34.9 | | GTG | 36.1 | 24.3 | 30.2 | 35.3 |
| | ATT | 34.0 | 49.6 | 41.8 | 41.8 | | GTT | 23.4 | 40.4 | 31.9 | 37.3 |

**NA = Not Applicable
***DNU = Do Not Use

TABLE 3

Codon compositions of coding regions for mature alpha toxin protein (370 amino acids). The native *C. perfringens* alpha toxin coding region is compared to a Plant-Optimized version containing three mutations.

| Amino Acid | Codon | Native Gene # | Native Gene % | Plnt Opt Gene # | Plnt Opt Gene % | Plnt Opt Recm'd |
|---|---|---|---|---|---|---|
| ALA (A) | GCA | 12 | 44.4 | 7 | 25.9 | 30.4 |
| | GCC | 0 | 0.0 | 9 | 33.3 | 30.2 |
| | GCG | 0 | 0.0 | 0 | 0.0 | DNU |
| | GCT | 15 | 55.6 | 11 | 40.7 | 39.4 |
| ARG (R) | AGA | 8 | 88.9 | 3 | 33.3 | 32.8 |
| | AGG | 1 | 11.1 | 3 | 33.3 | 32.6 |
| | CGA | 0 | 0.0 | 1 | 11.1 | 15.7 |
| | CGC | 0 | 0.0 | 0 | 0.0 | DNU |
| | CGG | 0 | 0.0 | 0 | 0.0 | DNU |
| | CGT | 0 | 0.0 | 2 | 22.2 | 19.0 |
| ASN (N) | AAC | 6 | 23.1 | 11 | 42.3 | 47.1 |
| | AAT | 20 | 76.9 | 15 | 57.7 | 52.9 |
| ASP (D) | GAC | 5 | 14.3 | 15 | 44.1 | 41.6 |
| | GAT | 30 | 85.7 | 19 | 55.9 | 58.4 |
| CYS (C) | TGC | 1 | 100.0 | 1 | 100.0 | 53.9 |
| | TGT | 0 | 0.0 | 0 | 0.0 | 46.1 |
| END | TAA | 1 | 100.0 | 0 | 0.0 | |
| | TAG | 0 | 0.0 | 0 | 0.0 | |
| | TGA | 0 | 0.0 | 1 | 100.0 | 1.0 |
| GLN (Q) | CAA | 9 | 81.8 | 6 | 54.5 | 50.0 |
| | CAG | 2 | 18.2 | 5 | 45.5 | 50.0 |
| GLU (E) | GAA | 14 | 63.6 | 10 | 47.6 | 46.3 |
| | GAG | 8 | 36.4 | 11 | 52.4 | 53.7 |
| GLY (G) | GGA | 16 | 64.0 | 8 | 29.6 | 28.0 |
| | GGC | 1 | 4.0 | 8 | 29.6 | 26.6 |
| | GGG | 2 | 8.0 | 3 | 11.1 | 18.9 |
| | GGT | 6 | 24.0 | 8 | 29.6 | 26.5 |
| HIS (H) | CAC | 2 | 22.2 | 5 | 62.5 | 46.4 |
| | CAT | 7 | 77.8 | 3 | 37.5 | 53.6 |
| ILE (J) | ATA | 11 | 50.0 | 5 | 22.7 | 23.3 |
| | ATC | 3 | 13.6 | 8 | 36.4 | 34.9 |
| | ATT | 8 | 36.4 | 9 | 40.9 | 41.8 |
| | Totals | 188 | | 187 | | |
| LEU (L) | CTA | 4 | 25.0 | 0 | 0.0 | DNU |
| | CTC | 0 | 0.0 | 4 | 23.5 | 25.6 |
| | CTG | 1 | 6.3 | 4 | 23.5 | 21.4 |
| | CTT | 2 | 12.5 | 4 | 23.5 | 27.0 |
| | TTA | 9 | 56.3 | 0 | 0.0 | DNU |
| | TTG | 0 | 0.0 | 5 | 29.4 | 26.0 |
| LYS (K) | AAA | 25 | 69.4 | 14 | 38.9 | 42.1 |
| | AAG | 11 | 30.6 | 22 | 61.1 | 57.9 |
| MET (M) | ATG | 8 | 100.0 | 8 | 100.0 | 100.0 |
| PHE (F) | TTC | 6 | 40.0 | 9 | 60.0 | 51.8 |
| | TTT | 9 | 60.0 | 6 | 40.0 | 48.2 |
| PRO (P) | CCA | 6 | 60.0 | 3 | 30.0 | 31.8 |
| | CCC | 0 | 0.0 | 2 | 20.0 | 17.3 |
| | CCG | 1 | 10.0 | 2 | 20.0 | 20.3 |
| | CCT | 3 | 30.0 | 3 | 30.0 | 30.6 |
| SER (S) | AGC | 0 | 0.0 | 4 | 16.7 | 18.5 |
| | AGT | 9 | 37.5 | 4 | 16.7 | 16.3 |
| | TCA | 11 | 45.8 | 6 | 25.0 | 21.5 |
| | TCC | 1 | 4.2 | 4 | 16.7 | 19.6 |
| | TCG | 0 | 0.0 | 0 | 0.0 | DNU |
| | TCT | 3 | 12.5 | 6 | 25.0 | 24.1 |
| THR (T) | ACA | 10 | 41.7 | 7 | 29.2 | 33.7 |
| | ACC | 0 | 0.0 | 6 | 25.0 | 29.6 |
| | ACG | 0 | 0.0 | 0 | 0.0 | DNU |
| | ACT | 14 | 58.3 | 11 | 45.8 | 36.8 |

TABLE 3-continued

Codon compositions of coding regions for mature alpha toxin protein (370 amino acids). The native *C. perfringens* alpha toxin coding region is compared to a Plant-Optimized version containing three mutations.

| Amino Acid | Codon | Native Gene # | Native Gene % | Plnt Opt Gene # | Plnt Opt Gene % | Plnt Opt Recm'd |
|---|---|---|---|---|---|---|
| TRP (W) | TGG | 10 | 100.0 | 10 | 100.0 | 100.0 |
| TYR (Y) | TAC | 4 | 15.4 | 14 | 53.8 | 50.1 |
|  | TAT | 22 | 84.6 | 12 | 46.2 | 49.9 |
| VAL (V) | GTA | 8 | 57.1 | 0 | 0.0 | DNU |
|  | GTC | 0 | 0.0 | 4 | 28.6 | 27.4 |
|  | GTG | 1 | 7.1 | 4 | 28.6 | 35.3 |
|  | GTT | 5 | 35.7 | 6 | 42.9 | 37.3 |
| Totals |  | 183 |  | 184 |  |  |

TABLE 4

Hemolytic activity endpoint of purified Mcpa samples and control.

| Sample or Standard | Lot Number | Hemolytic activity endpoint dilution/concentration |
|---|---|---|
| PLC Standard | 014K86152 | 0.265 units/mL |
| Mcpa | DAS F1041-188-2 | >500 µg/mL |
| NHT Mcpa | E2036-70-1072295 | 15.63 µg/mL |
| NHT Mcpa | E2036-88-96 | >500 µg/mL |

NHT = nontagged

TABLE 5

Clinical study design for evaluation of Mcpa antigens in young chickens.

| Group No | Antigen | Buffer | Adjuvant | Challenge | n = | Vaccine (dose/volume) |
|---|---|---|---|---|---|---|
| 1 | NA | NA | NA | No | 15 | NA |
| 2 | None | PBS | LAP/QAC (1:1) | Yes | 15 | None/0.5 mL |
| 3 | Tagged Mcpa (Pf) | PBS + 1 mM EDTA | LAP/QAC (1:1) | Yes | 15 | 40 mg/0.5 mL |
| 4 | Tagged Mcpa (Pf) | PBS + 1 mM EDTA | LAP/QAC (4:1) | Yes | 15 | 40 mg/0.5 mL |
| 5 | Nontagged Mcpa (Pf) | PBS + 1 mM EDTA | LAP/QAC (1:1) | Yes | 15 | 40 mg/0.5 mL |
| 6 | Nontagged Mcpa (Pf) | PBS + 1 mM EDTA | LAP/QAC (4:1) | Yes | 15 | 40 mg/0.5 mL |

PBS = phosphate buffered saline
LAP/QAC = Lecithin acrylic polymer plus Quil A cholesterol
SO = subcutaneous administration
LAP/QAC (1:1) = lecithin acrylic polymer and Quil A cholesterol (Quil A:cholesterol = 1:1 ratio by weight)
LAP/QAC (4:1) = lecithin acrylic polymer and Quil A cholesterol (Quil A:cholesterol = 4:1 ratio by weight)

TABLE 6

Lesion scores per treatment group.

| Group No | 0 | 1+ | 2+ | 3+ | 4+ | Not scorable* |
|---|---|---|---|---|---|---|
| 1 | 15 |  |  |  |  |  |
| 2 |  |  | 2 | 5 | 6 | 2 |
| 3 |  | 1 | 6 | 6 | 2 |  |
| 4 |  | 3 | 4 | 2 | 2 |  |
| 5 |  | 1 | 7 | 3 | 2 | 1 |
| 6 |  | 4 | 6 | 2 | 2 |  |

*death prior to study completion; gut autolysis prevented scoring

TABLE 7

Results of contingency analysis by lesion scores.

| Treatment group comparison | p value |
|---|---|
| PBS + challenged vs PBS + unchallenged | <.0001 |
| Mcpa + challenged LAP/QAC 1:1 vs PBS + unchallenged | <.0001 |
| Mcpa + challenged LAP/QAC 4:1 vs PBS + unchallenged | <.0001 |

TABLE 7-continued

Results of contingency analysis by lesion scores.

| Treatment group comparison | p value |
|---|---|
| nontagged Mcpa + challenged LAP/QAC 1:1 vs PBS + unchallenged | <.0001 |
| nontagged Mcpa + challenged LAP/QAC 4:1 vs PBS + unchallenged | <.0001 |
| Mcpa + challenged LAP/QAC 1:1 vs PBS + challenged | 0.1374 |
| Mcpa + challenged LAP/QAC 4:1 vs PBS + challenged | 0.0239 |
| nontagged Mcpa + challenged LAP/QAC 1:1 vs PBS + challenged | 0.0743 |
| nontagged Mcpa + challenged LAP/QAC 4:1 vs PBS + challenged | 0.0116 |
| Mcpa + challenged LAP/QAC 1:1 vs Mcpa + challenged LAP/QAC 4:1 | 0.4034 |
| Mcpa + challenged LAP/QAC 1:1 vs nontagged Mcpa + challenged LAP/QAC 1:1 | 0.8125 |
| Mcpa + challenged LAP/QAC 1:1 vs nontagged Mcpa + challenged LAP/QAC 4:1 | 0.2630 |
| Mcpa + challenged LAP/QAC 4:1 vs nontagged Mcpa + challenged LAP/QAC 1:1 | 0.5914 |
| Mcpa + challenged LAP/QAC 4:1 vs nontagged Mcpa + challenged LAP/QAC 4:1 | 0.9799 |
| nontagged Mcpa + challenged LAP/QAC 1:1 vs nontagged Mcpa + challenged LAP/QAC 4:1 | 0.5381 |

The invention claimed is:

1. A polynucleotide that encodes a protein comprising SEQ ID NO:4.

2. The polynucleotide of claim 1 comprising a sequence selected from the group consisting of SEQ ID NO:3, SEQ ID NO:7, SEQ ID NO:9, and SEQ ID NO:11.

3. A method of producing a protein encoded by the polynucleotide of claim 1, said method comprising constructing a plant expression vector comprising a nucleic acid sequence that encodes said protein, transforming a plant cell with said plant expression vector, culturing said transformed plant cell under conditions suitable for production of said protein, and enriching said protein from said transformed plant cell.

4. A method of producing protein encoded by the polynucleotide of claim 1, said method comprising constructing a prokaryotic expression vector comprising a polynucleotide that encodes said protein, transforming a prokaryotic cell with said prokaryotic expression vector, culturing said transformed prokaryotic cell under conditions suitable for production of said protein, and enriching said protein from said transformed prokaryotic cell.

5. The method of claim 4 wherein said prokaryotic cell is a *Pseudomonas fluorescens* cell.

6. An isolated polynucleotide that encodes a protein comprising residues 29 to 398 of SEQ ID NO:2.

7. The polynucleotide of claim 6 that encodes SEQ ID NO:2.

* * * * *

```
                      SEQUENCE LISTING

<160> NUMBER OF SEQ ID NOS: 16

<210> SEQ ID NO 1
<211> LENGTH: 1197
<212> TYPE: DNA
<213> ORGANISM: Clostridium perfringens
<220> FEATURE:
<221> NAME/KEY: misc_feature
<222> LOCATION: (1)..(1194)
<223> OTHER INFORMATION: Protein coding sequence
<220> FEATURE:
<221> NAME/KEY: misc_feature
<222> LOCATION: (1)..(84)
<223> OTHER INFORMATION: Encode native secretion signal peptide

<400> SEQUENCE: 1
atgaaaagaa agatttgtaa ggcacttatt tgtgctacgc tagcaactag cctatgggct     60
ggggcatcaa ctaaagtcta cgcttgggat ggaaagattg atggaacagg aactcatgct    120
atgattgtaa ctcaagggat ttcaatctta gaaaatgatc tgtccaaaaa tgaaccagaa    180
agtgtaagaa aaacttaga gatttttaaag cagaacatgc atgaacttca attaggttct    240
acttatccag attatgataa gaatgctat gatctatatc aagatcattt ctgggatcct     300
gatacagata taatttctc aaaggataat agttggtatt tagcttattc tatacctgat    360
acaggggaat cacaaataag aaaattttca gcattagcta gatatgaatg caaagagga    420 aactataaac aagctacatt ctatcttgga gaggctatgc actattttgg tgatatagat    480
actccatatc atcctgctaa tgttactgca gttgatagtg caggacatgt taagtttgag    540 actttttgcag aggaaagaaa agagcagtat aaaataaata cagcaggttg caaaactaat    600
gaggcttttt atgctgatat cttaaaaaac aaagatttta atgcatggtc aaaagaatat    660
gcaaggggtt ttgctaaaac aggaaaatca atatactaca gtcatgctag tatgagtcat    720
agttgggatg attgggatta tgcagcaaaa gtaactctag ctaactctca aaaaggaaca    780
gcaggatata tttatagatt cttacacgat gtatcagagg gtaatgatcc atcagttggc    840
aagaatgtaa aagaactagt agcttacata tcaactagtg gtgaaaaaga tgctggaaca    900
gatgactaca tgtattttgg aatcaaaaca aaggatggaa aaactcaaga atgggaaatg    960
gacaacccgg gaaatgactt tatgactgga agtaaagata cttatacttt caagttaaag   1020
gatgaaaatc taaaaattga tgacatacaa aatatgtgga ttagaaaaag aaaatataca   1080
```

-continued

```
gcattcccag atgcttataa gccagaaaat ataaaggtaa tagcaaatgg aaaagttgta    1140
gtggacaaag atataaatga gtggatttca ggaaattcaa cttataatat aaaataa      1197
```

<210> SEQ ID NO 2
<211> LENGTH: 398
<212> TYPE: PRT
<213> ORGANISM: Clostridium perfringens
<220> FEATURE:
<221> NAME/KEY: MISC_FEATURE
<222> LOCATION: (1)..(28)
<223> OTHER INFORMATION: Secretion signal peptide
<220> FEATURE:
<221> NAME/KEY: MISC_FEATURE
<222> LOCATION: (29)..(398)
<223> OTHER INFORMATION: Mature protein

<400> SEQUENCE: 2

```
Met Lys Arg Lys Ile Cys Lys Ala Leu Ile Cys Ala Thr Leu Ala Thr
1               5                   10                  15

Ser Leu Trp Ala Gly Ala Ser Thr Lys Val Tyr Ala Trp Asp Gly Lys
            20                  25                  30

Ile Asp Gly Thr Gly Thr His Ala Met Ile Val Thr Gln Gly Ile Ser
        35                  40                  45

Ile Leu Glu Asn Asp Leu Ser Lys Asn Glu Pro Glu Ser Val Arg Lys
    50                  55                  60

Asn Leu Glu Ile Leu Lys Gln Asn Met His Glu Leu Gln Leu Gly Ser
65                  70                  75                  80

Thr Tyr Pro Asp Tyr Asp Lys Asn Ala Tyr Asp Leu Tyr Gln Asp His
                85                  90                  95

Phe Trp Asp Pro Asp Thr Asp Asn Asn Phe Ser Lys Asp Asn Ser Trp
            100                 105                 110

Tyr Leu Ala Tyr Ser Ile Pro Asp Thr Gly Glu Ser Gln Ile Arg Lys
        115                 120                 125

Phe Ser Ala Leu Ala Arg Tyr Glu Trp Gln Arg Gly Asn Tyr Lys Gln
    130                 135                 140

Ala Thr Phe Tyr Leu Gly Glu Ala Met His Tyr Phe Gly Asp Ile Asp
145                 150                 155                 160

Thr Pro Tyr His Pro Ala Asn Val Thr Ala Val Asp Ser Ala Gly His
                165                 170                 175

Val Lys Phe Glu Thr Phe Ala Glu Glu Arg Lys Glu Gln Tyr Lys Ile
            180                 185                 190

Asn Thr Ala Gly Cys Lys Thr Asn Glu Ala Phe Tyr Ala Asp Ile Leu
        195                 200                 205

Lys Asn Lys Asp Phe Asn Ala Trp Ser Lys Glu Tyr Ala Arg Gly Phe
    210                 215                 220

Ala Lys Thr Gly Lys Ser Ile Tyr Tyr Ser His Ala Ser Met Ser His
225                 230                 235                 240

Ser Trp Asp Asp Trp Asp Tyr Ala Ala Lys Val Thr Leu Ala Asn Ser
                245                 250                 255

Gln Lys Gly Thr Ala Gly Tyr Ile Tyr Arg Phe Leu His Asp Val Ser
            260                 265                 270

Glu Gly Asn Asp Pro Ser Val Gly Lys Asn Val Lys Glu Leu Val Ala
        275                 280                 285

Tyr Ile Ser Thr Ser Gly Glu Lys Asp Ala Gly Thr Asp Asp Tyr Met
    290                 295                 300

Tyr Phe Gly Ile Lys Thr Lys Asp Gly Lys Thr Gln Glu Trp Glu Met
305                 310                 315                 320
```

-continued

```
Asp Asn Pro Gly Asn Asp Phe Met Thr Gly Ser Lys Asp Thr Tyr Thr
            325                 330                 335

Phe Lys Leu Lys Asp Glu Asn Leu Lys Ile Asp Asp Ile Gln Asn Met
        340                 345                 350

Trp Ile Arg Lys Arg Lys Tyr Thr Ala Phe Pro Asp Ala Tyr Lys Pro
    355                 360                 365

Glu Asn Ile Lys Val Ile Ala Asn Gly Lys Val Val Asp Lys Asp
    370                 375                 380

Ile Asn Glu Trp Ile Ser Gly Asn Ser Thr Tyr Asn Ile Lys
385                 390                 395

<210> SEQ ID NO 3
<211> LENGTH: 1113
<212> TYPE: DNA
<213> ORGANISM: Clostridium perfringens
<220> FEATURE:
<221> NAME/KEY: misc_feature
<222> LOCATION: (1)..(1211)
<223> OTHER INFORMATION: Mutant Clostridium perfringens phospholipase C
      isolated from a chicken with ER targeting and retention signals.
      This DNA sequence has reworked codon usage optimized for
      expression in tobacco and rice
<220> FEATURE:
<221> NAME/KEY: misc_feature
<222> LOCATION: (1)..(63)
<223> OTHER INFORMATION: Encode 15 kDa Zein Endoplasmic Reticulum
      targeting signal
<220> FEATURE:
<221> NAME/KEY: misc_feature
<222> LOCATION: (229)..(231)
<223> OTHER INFORMATION: Encode Mutation D84L (Aspartic acid to Leucine
      at amino acid 84 of native protein)
<220> FEATURE:
<221> NAME/KEY: misc_feature
<222> LOCATION: (505)..(507)
<223> OTHER INFORMATION: Encode Mutation H176G (Histidine to Glycine at
      amino acid 176 of native protein)
<220> FEATURE:
<221> NAME/KEY: misc_feature
<222> LOCATION: (517)..(519)
<223> OTHER INFORMATION: Encode Mutation E180G (Glutamic acid to Glycine
      at amino acid 180 of native protein)
<220> FEATURE:
<221> NAME/KEY: misc_feature
<222> LOCATION: (1171)..(1182)
<223> OTHER INFORMATION: Encode KDEL Endoplasmic Reticulum retention
      signal
<220> FEATURE:
<221> NAME/KEY: misc_feature
<222> LOCATION: (1185)..(1211)
<223> OTHER INFORMATION: Six-frame translation stops

<400> SEQUENCE: 3
tgggatggaa agattgatgg cactggcact catgccatga ttgtgactca agggatttcc      60
atcttggaaa tgacctctc caagaatgag ccagaaagtg tgaggaagaa cctggagatt     120
ttgaagcaga acatgcatga actccagctt ggttctacct atccgttgta tgacaagaat    180
gcttatgatc tgtaccaaga tcacttctgg gaccctgata cagataacaa tttcagcaag    240
gacaactcat ggtacctggc ttattcaatt ccagacaccg gggaatccca gataaggaag    300
ttctctgcac ttgcaagata tgaatggcaa cgtggcaact acaaacaagc aacattctat    360
cttggtgagg ccatgcacta ctttggtgat atagacacac cctaccaccc tgccaatgtc    420
actgctgttg acagtgctgg cggtgttaag tttgggacct tgctgaaga gagaaaagag    480 cagtacaaga taaacacagc aggctgcaaa acaaatgagg cttctatgc tgacatcttg    540 aagaacaaag atttcaatgc ctggtcaaaa gagtatgcca gaggttttgc caaaactgga    600
```

```
aaatccatct attacagcca tgccagcatg agccacagtt gggatgactg ggattatgct    660
gcaaaagtta ctttggcaaa ctctcagaaa ggaactgctg gttacatcta ccgattcctc    720
catgatgtca gtgagggcaa tgatccctct gttggcaaga atgtgaaaga gcttgttgct    780
tacatatcaa cttctggtga aaagatgct ggaactgatg actacatgta tttcggaatc    840
aagacaaagg atgaaagac ccaagaatgg gaaatggaca cccctggaaa tgactttatg    900
acaggttcaa aggacactta cactttcaag ctgaaggatg aaaatctcaa gattgatgac    960
attcaaaaca tgtggattcg taaaaggaaa tacacagcat ttccagatgc ctataagccg    1020
gaaaacatca aggtcatagc aaatggaaag gttgtcgtgg acaaggatat caatgagtgg    1080
atttctggca attcaaccta caatatcaaa tga                                  1113
```

<210> SEQ ID NO 4
<211> LENGTH: 370
<212> TYPE: PRT
<213> ORGANISM: Clostridium perfringens
<220> FEATURE:
<221> NAME/KEY: MISC_FEATURE
<222> LOCATION: (56)..(56)
<223> OTHER INFORMATION: D56L mutated residue
<220> FEATURE:
<221> NAME/KEY: MISC_FEATURE
<222> LOCATION: (148)..(148)
<223> OTHER INFORMATION: H148G mutated residue
<220> FEATURE:
<221> NAME/KEY: MISC_FEATURE
<222> LOCATION: (152)..(152)
<223> OTHER INFORMATION: E152G mutated residue

<400> SEQUENCE: 4

```
Trp Asp Gly Lys Ile Asp Gly Thr Gly Thr His Ala Met Ile Val Thr
1               5                   10                  15

Gln Gly Ile Ser Ile Leu Glu Asn Asp Leu Ser Lys Asn Glu Pro Glu
            20                  25                  30

Ser Val Arg Lys Asn Leu Glu Ile Leu Lys Gln Asn Met His Glu Leu
        35                  40                  45

Gln Leu Gly Ser Thr Tyr Pro Leu Tyr Asp Lys Asn Ala Tyr Asp Leu
    50                  55                  60

Tyr Gln Asp His Phe Trp Asp Pro Asp Thr Asp Asn Asn Phe Ser Lys
65                  70                  75                  80

Asp Asn Ser Trp Tyr Leu Ala Tyr Ser Ile Pro Asp Thr Gly Glu Ser
                85                  90                  95

Gln Ile Arg Lys Phe Ser Ala Leu Ala Arg Tyr Glu Trp Gln Arg Gly
            100                 105                 110

Asn Tyr Lys Gln Ala Thr Phe Tyr Leu Gly Glu Ala Met His Tyr Phe
        115                 120                 125

Gly Asp Ile Asp Thr Pro Tyr His Pro Ala Asn Val Thr Ala Val Asp
    130                 135                 140

Ser Ala Gly Gly Val Lys Phe Gly Thr Phe Ala Glu Glu Arg Lys Glu
145                 150                 155                 160

Gln Tyr Lys Ile Asn Thr Ala Gly Cys Lys Thr Asn Glu Ala Phe Tyr
                165                 170                 175

Ala Asp Ile Leu Lys Asn Lys Asp Phe Asn Ala Trp Ser Lys Glu Tyr
            180                 185                 190

Ala Arg Gly Phe Ala Lys Thr Gly Lys Ser Ile Tyr Tyr Ser His Ala
        195                 200                 205

Ser Met Ser His Ser Trp Asp Asp Trp Asp Tyr Ala Ala Lys Val Thr
```

-continued

```
            210                 215                 220
Leu Ala Asn Ser Gln Lys Gly Thr Ala Gly Tyr Ile Tyr Arg Phe Leu
225                 230                 235                 240

His Asp Val Ser Glu Gly Asn Asp Pro Ser Val Gly Lys Asn Val Lys
                245                 250                 255

Glu Leu Val Ala Tyr Ile Ser Thr Ser Gly Glu Lys Asp Ala Gly Thr
            260                 265                 270

Asp Asp Tyr Met Tyr Phe Gly Ile Lys Thr Lys Asp Gly Lys Thr Gln
                275                 280                 285

Glu Trp Glu Met Asp Asn Pro Gly Asn Asp Phe Met Thr Gly Ser Lys
290                 295                 300

Asp Thr Tyr Thr Phe Lys Leu Lys Asp Glu Asn Leu Lys Ile Asp Asp
305                 310                 315                 320

Ile Gln Asn Met Trp Ile Arg Lys Arg Lys Tyr Thr Ala Phe Pro Asp
                325                 330                 335

Ala Tyr Lys Pro Glu Asn Ile Lys Val Ile Ala Asn Gly Lys Val Val
                340                 345                 350

Val Asp Lys Asp Ile Asn Glu Trp Ile Ser Gly Asn Ser Thr Tyr Asn
            355                 360                 365

Ile Lys
    370
```

<210> SEQ ID NO 5
<211> LENGTH: 63
<212> TYPE: DNA
<213> ORGANISM: Artificial sequence
<220> FEATURE:
<223> OTHER INFORMATION: Chemically synthesized plant-optimized DNA
      sequence for modified 15 kDa zein Endoplasmic Reticulum targeting
      peptide

<400> SEQUENCE: 5
atggctaaga tggtcattgt gcttgttgtg tgcttggctc tctctgctgc ctcagcttct    60
gcc                                                                 63

<210> SEQ ID NO 6
<211> LENGTH: 21
<212> TYPE: PRT
<213> ORGANISM: Artificial sequence
<220> FEATURE:
<223> OTHER INFORMATION: Chemically synthesized amino acid sequence of
      modified 15 kDa zein Endoplasmic Reticulum targeting peptide
      encoded by SEQ ID NO:5

<400> SEQUENCE: 6

```
Met Ala Lys Met Val Ile Val Leu Val Val Cys Leu Ala Leu Ser Ala
1               5                   10                  15

Ala Ser Ala Ser Ala
            20
```

<210> SEQ ID NO 7
<211> LENGTH: 1185
<212> TYPE: DNA
<213> ORGANISM: Artificial sequence
<220> FEATURE:
<223> OTHER INFORMATION: Chemically synthesized plant-optimized DNA
      sequence encoding mature mutated C. perfringens alpha toxin
      protein with 15 kDA zein endoplasmic reticulum targeting peptide,
      and KDEL ER retention peptide.
<220> FEATURE:
<221> NAME/KEY: misc_feature
<222> LOCATION: (1)..(63)

<223> OTHER INFORMATION: 15 kDa zein ER targeting peptide
<220> FEATURE:
<221> NAME/KEY: misc_feature
<222> LOCATION: (64)..(1173)
<223> OTHER INFORMATION: mutated mature C. perfringens alpha toxin
      protein
<220> FEATURE:
<221> NAME/KEY: misc_feature
<222> LOCATION: (1171)..(1182)
<223> OTHER INFORMATION: KDEL ER retention peptide

<400> SEQUENCE: 7

| | | | | | |
|---|---|---|---|---|---|
| atggctaaga | tggtcattgt | gcttgttgtg | tgcttggctc | tctctgctgc | ctcagcttct | 60 |
| gcctgggatg | gaaagattga | tggcactggc | actcatgcca | tgattgtgac | tcaagggatt | 120 |
| tccatcttgg | aaaatgacct | ctccaagaat | gagccagaaa | gtgtgaggaa | gaacctggag | 180 |
| attttgaagc | agaacatgca | cgaactccag | cttggttcta | cctatccgtt | gtatgacaag | 240 |
| aatgcttatg | atctgtacca | agatcacttc | tgggaccctg | atacagataa | caatttcagc | 300 |
| aaggacaact | catggtacct | ggcttattca | attccagaca | ccggggaatc | ccagataagg | 360 |
| aagttctctg | cacttgcaag | atatgaatgg | caacgtggca | actacaaaca | agcaacattc | 420 |
| tatcttggtg | aggccatgca | ctactttggt | gatatagaca | caccctacca | ccctgccaat | 480 |
| gtcactgctg | ttgacagtgc | tggcggtgtt | aagtttggga | cctttgctga | agagagaaaa | 540 |
| gagcagtaca | agataaacac | agccggctgc | aaaacaaatg | aggctttcta | tgctgacatc | 600 |
| ttgaagaaca | aagatttcaa | tgcctggtca | aagagtatgc | cagaggtttt | gccaaaact | 660 |
| ggaaaatcca | tctattacag | ccatgccagc | atgagccaca | gttgggatga | ctgggattat | 720 |
| gctgcaaaag | ttactttggc | aaactctcag | aaaggaactg | ctggttacat | ctaccgattc | 780 |
| ctccatgatg | tcagtgaggg | caatgatccc | tctgttggca | agaatgtgaa | agagcttgtt | 840 |
| gcttacatat | caacttctgg | tgagaaagat | gctggaactg | atgactacat | gtatttcgga | 900 |
| atcaagacaa | aggatggaaa | gacccaagaa | tgggaaatgg | acaaccctgg | aaatgacttt | 960 |
| atgaccggtt | caaaggacac | ttacactttc | aagctgaagg | atgaaaatct | caagattgat | 1020 |
| gacattcaaa | acatgtggat | tcgtaaaagg | aaatacacag | catttccaga | tgcctataag | 1080 |
| ccggaaaaca | tcaaggtcat | agcaaatgga | aaggttgtcg | tggacaagga | tatcaatgag | 1140 |
| tggatttctg | gcaattcaac | ctacaatatc | aaagatgagc | tttga | | 1185 |

<210> SEQ ID NO 8
<211> LENGTH: 394
<212> TYPE: PRT
<213> ORGANISM: Artificial sequence
<220> FEATURE:
<223> OTHER INFORMATION: Chemically synthesized fusion protein of mature
      mutated C. perfringens alpha toxin protein with 15 kDA zein
      endoplasmic reticulum targeting peptide, and KDEL ER retention
      peptide
<220> FEATURE:
<221> NAME/KEY: misc_feature
<222> LOCATION: (1)..(21)
<223> OTHER INFORMATION: 15 kDa zein ER targeting peptide
<220> FEATURE:
<221> NAME/KEY: misc_feature
<222> LOCATION: (22)..(391)
<223> OTHER INFORMATION: mutated mature C. perfringens alpha toxin
      protein
<220> FEATURE:
<221> NAME/KEY: misc_feature
<222> LOCATION: (391)..(394)
<223> OTHER INFORMATION: KDEL ER retention peptide

<400> SEQUENCE: 8

```
Met Ala Lys Met Val Ile Val Leu Val Val Cys Leu Ala Leu Ser Ala
1               5                   10                  15

Ala Ser Ala Ser Ala Trp Asp Gly Lys Ile Asp Gly Thr Gly Thr His
            20                  25                  30

Ala Met Ile Val Thr Gln Gly Ile Ser Ile Leu Glu Asn Asp Leu Ser
        35                  40                  45

Lys Asn Glu Pro Glu Ser Val Arg Lys Asn Leu Glu Ile Leu Lys Gln
50                  55                  60

Asn Met His Glu Leu Gln Leu Gly Ser Thr Tyr Pro Leu Tyr Asp Lys
65                  70                  75                  80

Asn Ala Tyr Asp Leu Tyr Gln Asp His Phe Trp Asp Pro Asp Thr Asp
                85                  90                  95

Asn Asn Phe Ser Lys Asp Asn Ser Trp Tyr Leu Ala Tyr Ser Ile Pro
            100                 105                 110

Asp Thr Gly Glu Ser Gln Ile Arg Lys Phe Ser Ala Leu Ala Arg Tyr
        115                 120                 125

Glu Trp Gln Arg Gly Asn Tyr Lys Gln Ala Thr Phe Tyr Leu Gly Glu
    130                 135                 140

Ala Met His Tyr Phe Gly Asp Ile Asp Thr Pro Tyr His Pro Ala Asn
145                 150                 155                 160

Val Thr Ala Val Asp Ser Ala Gly Gly Val Lys Phe Gly Thr Phe Ala
                165                 170                 175

Glu Glu Arg Lys Glu Gln Tyr Lys Ile Asn Thr Ala Gly Cys Lys Thr
            180                 185                 190

Asn Glu Ala Phe Tyr Ala Asp Ile Leu Lys Asn Lys Asp Phe Asn Ala
        195                 200                 205

Trp Ser Lys Glu Tyr Ala Arg Gly Phe Ala Lys Thr Gly Lys Ser Ile
    210                 215                 220

Tyr Tyr Ser His Ala Ser Met Ser His Ser Trp Asp Trp Asp Tyr
225                 230                 235                 240

Ala Ala Lys Val Thr Leu Ala Asn Ser Gln Lys Gly Thr Ala Gly Tyr
                245                 250                 255

Ile Tyr Arg Phe Leu His Asp Val Ser Glu Gly Asn Asp Pro Ser Val
            260                 265                 270

Gly Lys Asn Val Lys Glu Leu Val Ala Tyr Ile Ser Thr Ser Gly Glu
        275                 280                 285

Lys Asp Ala Gly Thr Asp Asp Tyr Met Tyr Phe Gly Ile Lys Thr Lys
    290                 295                 300

Asp Gly Lys Thr Gln Glu Trp Glu Met Asp Asn Pro Gly Asn Asp Phe
305                 310                 315                 320

Met Thr Gly Ser Lys Asp Thr Tyr Thr Phe Lys Leu Lys Asp Glu Asn
                325                 330                 335

Leu Lys Ile Asp Asp Ile Gln Asn Met Trp Ile Arg Lys Arg Lys Tyr
            340                 345                 350

Thr Ala Phe Pro Asp Ala Tyr Lys Pro Glu Asn Ile Lys Val Ile Ala
        355                 360                 365

Asn Gly Lys Val Val Asp Lys Asp Ile Asn Glu Trp Ile Ser Gly
    370                 375                 380

Asn Ser Thr Tyr Asn Ile Lys Asp Glu Leu
385                 390

<210> SEQ ID NO 9
<211> LENGTH: 1269
<212> TYPE: DNA
```

<213> ORGANISM: Artificial sequence
<220> FEATURE:
<223> OTHER INFORMATION: Encodes mutant phospholipase C with his-tag, thrombin recognition site, S-tag and enterokinase recognition site
<220> FEATURE:
<221> NAME/KEY: misc_feature
<222> LOCATION: (1)..(1269)
<223> OTHER INFORMATION: Protein coding sequence
<220> FEATURE:
<221> NAME/KEY: misc_feature
<222> LOCATION: (1)..(159)
<223> OTHER INFORMATION: Sequence coding for his-tag, thrombin recognition site, S-tag and enterokinase recognition site
<220> FEATURE:
<221> NAME/KEY: misc_feature
<222> LOCATION: (325)..(327)
<223> OTHER INFORMATION: Encode Mutation D84L (Aspartic acid to Leucine at amino acid 84 of native protein)
<220> FEATURE:
<221> NAME/KEY: misc_feature
<222> LOCATION: (601)..(603)
<223> OTHER INFORMATION: Encode Mutation H176G (Histidine to Glycine at amino acid 176 of native protein)
<220> FEATURE:
<221> NAME/KEY: misc_feature
<222> LOCATION: (613)..(615)
<223> OTHER INFORMATION: Encode Mutation E180G (Glutamic acid to Glycine at amino acid 180 of native protein)

<400> SEQUENCE: 9

```
atgcatcacc atcaccatca ctccgcgggt ctggtgccac gcggtagtac tgcaattggt      60
atgaaagaaa ccgctgctgc taaattcgaa cgccagcaca tggacagccc agatctgggt    120
accggtggtg gctccggtga tgacgacgac aagagtccat gggatggaaa gattgatggc    180
actggcactc atgccatgat tgtgactcaa gggatttcca tcttggaaaa tgacctctcc    240
aagaatgagc agaaagtgt gaggaagaac ctggagattt tgaagcagaa catgcacgaa    300
ctccagcttg gttctaccta tccgttgtat gacaagaatg cttatgatct gtaccaagat    360
cacttctggg accctgatac agataacaat ttcagcaagg acaactcatg gtacctggct    420
tattcaattc agacaccgg ggaatcccag ataaggaagt tctctgcact tgcaagatat    480
gaatggcaac gtggcaacta caaacaagca acattctatc ttggtgaggc catgcactac    540
tttggtgata tagacacacc ctaccaccct gccaatgtca ctgctgttga cagtgctggc    600
ggtgttaagt ttgggaccct tgctgaagag agaaaagagc agtacaagat aaacacagcc    660
ggctgcaaaa caaatgaggc tttctatgct gacatcttga agaacaaaga tttcaatgcc    720
tggtcaaaag agtatgccag aggttttgcc aaaactggaa atccatcta ttacagccat    780
gccagcatga gccacagttg ggatgactgg gattatgctg caaagttac tttggcaaac    840
tctcagaaag gaactgctgg ttacatctac cgattcctcc atgatgtcag tgagggcaat    900
gatccctctg ttggcaagaa tgtgaaagag cttgttgctt acatatcaac ttctggtgag    960
aaagatgctg gaactgatga ctacatgtat tcggaatca agacaaagga tggaaagacc   1020
caagaatggg aaatggacaa ccctggaaat gactttatga ccggttcaaa ggacacttac   1080
actttcaagc tgaaggatga aaatctcaag attgatgaca ttcaaaacat gtggattcgt   1140
aaaaggaaat acacagcatt tccagatgcc tataagccgg aaaacatcaa ggtcatagca   1200
aatggaaagg ttgtcgtgga caaggatatc aatgagtgga tttctggcaa ttcaacctac   1260
aatatcaaa                                                          1269
```

<210> SEQ ID NO 10
<211> LENGTH: 423
<212> TYPE: PRT

```
<213> ORGANISM: Artificial sequence
<220> FEATURE:
<223> OTHER INFORMATION: Chemically synthesized protein encoded by SEQ
      ID NO:9
<220> FEATURE:
<221> NAME/KEY: misc_feature
<222> LOCATION: (1)..(423)
<223> OTHER INFORMATION: mutant phospholipase C with his-tag, thrombin
      recognition site, S-tag and enterokinase recognition site
<220> FEATURE:
<221> NAME/KEY: misc_feature
<222> LOCATION: (1)..(53)
<223> OTHER INFORMATION: his-tag, thrombin recognition site, S-tag and
      enterokinase recognition site
<220> FEATURE:
<221> NAME/KEY: misc_feature
<222> LOCATION: (109)..(109)
<223> OTHER INFORMATION: Mutation D84L (Aspartic acid to Leucine at
      amino acid 84 of native protein)
<220> FEATURE:
<221> NAME/KEY: misc_feature
<222> LOCATION: (201)..(201)
<223> OTHER INFORMATION: Mutation H176G (Histidine to Glycine at amino
      acid 176 of native protein)
<220> FEATURE:
<221> NAME/KEY: misc_feature
<222> LOCATION: (205)..(205)
<223> OTHER INFORMATION: Mutation E180G (Glutamic acid to Glycine at
      amino acid 180 of native protein)

<400> SEQUENCE: 10

Met His His His His His His Ser Ala Gly Leu Val Pro Arg Gly Ser
1               5                   10                  15

Thr Ala Ile Gly Met Lys Glu Thr Ala Ala Ala Lys Phe Glu Arg Gln
            20                  25                  30

His Met Asp Ser Pro Asp Leu Gly Thr Gly Gly Gly Ser Gly Asp Asp
        35                  40                  45

Asp Asp Lys Ser Pro Trp Asp Gly Lys Ile Asp Gly Thr Gly Thr His
    50                  55                  60

Ala Met Ile Val Thr Gln Gly Ile Ser Ile Leu Glu Asn Asp Leu Ser
65                  70                  75                  80

Lys Asn Glu Pro Glu Ser Val Arg Lys Asn Leu Glu Ile Leu Lys Gln
                85                  90                  95

Asn Met His Glu Leu Gln Leu Gly Ser Thr Tyr Pro Leu Tyr Asp Lys
            100                 105                 110

Asn Ala Tyr Asp Leu Tyr Gln Asp His Phe Trp Asp Pro Asp Thr Asp
        115                 120                 125

Asn Asn Phe Ser Lys Asp Asn Ser Trp Tyr Leu Ala Tyr Ser Ile Pro
    130                 135                 140

Asp Thr Gly Glu Ser Gln Ile Arg Lys Phe Ser Ala Leu Ala Arg Tyr
145                 150                 155                 160

Glu Trp Gln Arg Gly Asn Tyr Lys Gln Ala Thr Phe Tyr Leu Gly Glu
                165                 170                 175

Ala Met His Tyr Phe Gly Asp Ile Asp Thr Pro Tyr His Pro Ala Asn
            180                 185                 190

Val Thr Ala Val Asp Ser Ala Gly Gly Val Lys Phe Gly Thr Phe Ala
        195                 200                 205

Glu Glu Arg Lys Glu Gln Tyr Lys Ile Asn Thr Ala Gly Cys Lys Thr
    210                 215                 220

Asn Glu Ala Phe Tyr Ala Asp Ile Leu Lys Asn Lys Asp Phe Asn Ala
225                 230                 235                 240

Trp Ser Lys Glu Tyr Ala Arg Gly Phe Ala Lys Thr Gly Lys Ser Ile
                245                 250                 255
```

-continued

```
Tyr Tyr Ser His Ala Ser Met Ser His Ser Trp Asp Asp Trp Asp Tyr
            260                 265                 270

Ala Ala Lys Val Thr Leu Ala Asn Ser Gln Lys Gly Thr Ala Gly Tyr
        275                 280                 285

Ile Tyr Arg Phe Leu His Asp Val Ser Glu Gly Asn Asp Pro Ser Val
    290                 295                 300

Gly Lys Asn Val Lys Glu Leu Val Ala Tyr Ile Ser Thr Ser Gly Glu
305                 310                 315                 320

Lys Asp Ala Gly Thr Asp Asp Tyr Met Tyr Phe Gly Ile Lys Thr Lys
                325                 330                 335

Asp Gly Lys Thr Gln Glu Trp Glu Met Asp Asn Pro Gly Asn Asp Phe
            340                 345                 350

Met Thr Gly Ser Lys Asp Thr Tyr Thr Phe Lys Leu Lys Asp Glu Asn
        355                 360                 365

Leu Lys Ile Asp Asp Ile Gln Asn Met Trp Ile Arg Lys Arg Lys Tyr
    370                 375                 380

Thr Ala Phe Pro Asp Ala Tyr Lys Pro Glu Asn Ile Lys Val Ile Ala
385                 390                 395                 400

Asn Gly Lys Val Val Asp Lys Asp Ile Asn Glu Trp Ile Ser Gly
                405                 410                 415

Asn Ser Thr Tyr Asn Ile Lys
            420

<210> SEQ ID NO 11
<211> LENGTH: 1116
<212> TYPE: DNA
<213> ORGANISM: Artificial sequence
<220> FEATURE:
<223> OTHER INFORMATION: Encodes mutant phospholipase C with two extra
      amino acids
<220> FEATURE:
<221> NAME/KEY: misc_feature
<222> LOCATION: (1)..(1116)
<223> OTHER INFORMATION: Protein coding sequence
<220> FEATURE:
<221> NAME/KEY: misc_feature
<222> LOCATION: (1)..(6)
<223> OTHER INFORMATION: Sequence coding for two amino acids introduced
      during PCR amplification
<220> FEATURE:
<221> NAME/KEY: misc_feature
<222> LOCATION: (172)..(174)
<223> OTHER INFORMATION: Encode Mutation D84L (Aspartic acid to Leucine
      at amino acid 84 of native protein)
<220> FEATURE:
<221> NAME/KEY: misc_feature
<222> LOCATION: (448)..(450)
<223> OTHER INFORMATION: Encode Mutation H176G (Histidine to Glycine at
      amino acid 176 of native protein)
<220> FEATURE:
<221> NAME/KEY: misc_feature
<222> LOCATION: (460)..(462)
<223> OTHER INFORMATION: Encode Mutation E180G (Glutamic acid to Glycine
      at amino acid 180 of native protein)

<400> SEQUENCE: 11
atgagttggg atggaaagat tgatggcact ggcactcatg ccatgattgt gactcaaggg      60
atttccatct tggaaaatga cctctccaag aatgagccag aaagtgtgag gaagaacctg     120
gagattttga gcagaacat gcacgaactc cagcttggtt ctacctatcc gttgtatgac     180
aagaatgctt atgatctgta ccaagatcac ttctgggacc ctgatacaga taacaatttc     240
agcaaggaca actcatggta cctggcttat tcaattccag acaccgggga atcccagata     300
```

-continued

```
aggaagttct ctgcacttgc aagatatgaa tggcaacgtg gcaactacaa acaagcaaca      360
ttctatcttg gtgaggccat gcactacttt ggtgatatag acacaccta ccaccctgcc       420 aatgtcactg ctgttgacag tgctggcggt gttaagtttg ggacctttgc tgaagagaga      480
aaagagcagt acaagataaa cacagccggc tgcaaaacaa atgaggcttt ctatgctgac      540
atcttgaaga acaaagattt caatgcctgg tcaaaagagt atgccagagg ttttgccaaa      600
actggaaaat ccatctatta cagccatgcc agcatgagcc acagttggga tgactgggat      660
tatgctgcaa aagttacttt ggcaaactct cagaaaggaa ctgctggtta catctaccga      720
ttcctccatg atgtcagtga gggcaatgat ccctctgttg caagaatgt gaaagagctt       780 gttgcttaca tatcaacttc tggtgagaaa gatgctggaa ctgatgacta catgtatttc      840
ggaatcaaga caaaggatgg aaagacccaa gaatgggaaa tggacaaccc tggaaatgac      900
tttatgaccg gttcaaagga cacttacact ttcaagctga aggatgaaaa tctcaagatt      960
gatgacattc aaaacatgtg gattcgtaaa aggaaataca cagcatttcc agatgcctat     1020
aagccggaaa acatcaaggt catagcaaat ggaaaggttg tcgtggacaa ggatatcaat     1080
gagtggattt ctggcaattc aacctacaat atcaaa                               1116
```

<210> SEQ ID NO 12
<211> LENGTH: 372
<212> TYPE: PRT
<213> ORGANISM: Artificial sequence
<220> FEATURE:
<223> OTHER INFORMATION: Chemically synthesized protein encoded by SEQ
      ID NO:11
<220> FEATURE:
<221> NAME/KEY: MISC_FEATURE
<222> LOCATION: (1)..(423)
<223> OTHER INFORMATION: mutant phospholipase C with two extra amino
      acids
<220> FEATURE:
<221> NAME/KEY: MISC_FEATURE
<222> LOCATION: (1)..(2)
<223> OTHER INFORMATION: two amino acids introduced during PCR
      amplification
<220> FEATURE:
<221> NAME/KEY: MISC_FEATURE
<222> LOCATION: (58)..(58)
<223> OTHER INFORMATION: Mutation D84L (Aspartic acid to Leucine at
      amino acid 84 of native protein)
<220> FEATURE:
<221> NAME/KEY: MISC_FEATURE
<222> LOCATION: (150)..(150)
<223> OTHER INFORMATION: Mutation H176G (Histidine to Glycine at amino
      acid 176 of native protein)
<220> FEATURE:
<221> NAME/KEY: MISC_FEATURE
<222> LOCATION: (154)..(154)
<223> OTHER INFORMATION: Mutation E180G (Glutamic acid to Glycine at
      amino acid 180 of native protein)

<400> SEQUENCE: 12

Met Ser Trp Asp Gly Lys Ile Asp Gly Thr Gly Thr His Ala Met Ile
1               5                   10                  15

Val Thr Gln Gly Ile Ser Ile Leu Glu Asn Asp Leu Ser Lys Asn Glu
            20                  25                  30

Pro Glu Ser Val Arg Lys Asn Leu Glu Ile Leu Lys Gln Asn Met His
        35                  40                  45

Glu Leu Gln Leu Gly Ser Thr Tyr Pro Leu Tyr Asp Lys Asn Ala Tyr
    50                  55                  60

Asp Leu Tyr Gln Asp His Phe Trp Asp Pro Asp Thr Asp Asn Asn Phe
65                  70                  75                  80

```
Ser Lys Asp Asn Ser Trp Tyr Leu Ala Tyr Ser Ile Pro Asp Thr Gly
            85                  90                  95

Glu Ser Gln Ile Arg Lys Phe Ser Ala Leu Ala Arg Tyr Glu Trp Gln
        100                 105                 110

Arg Gly Asn Tyr Lys Gln Ala Thr Phe Tyr Leu Gly Glu Ala Met His
    115                 120                 125

Tyr Phe Gly Asp Ile Asp Thr Pro Tyr His Pro Ala Asn Val Thr Ala
130                 135                 140

Val Asp Ser Ala Gly Gly Val Lys Phe Gly Thr Phe Ala Glu Glu Arg
145                 150                 155                 160

Lys Glu Gln Tyr Lys Ile Asn Thr Ala Gly Cys Lys Thr Asn Glu Ala
                165                 170                 175

Phe Tyr Ala Asp Ile Leu Lys Asn Lys Asp Phe Asn Ala Trp Ser Lys
            180                 185                 190

Glu Tyr Ala Arg Gly Phe Ala Lys Thr Gly Lys Ser Ile Tyr Tyr Ser
        195                 200                 205

His Ala Ser Met Ser His Ser Trp Asp Asp Trp Asp Tyr Ala Ala Lys
    210                 215                 220

Val Thr Leu Ala Asn Ser Gln Lys Gly Thr Ala Gly Tyr Ile Tyr Arg
225                 230                 235                 240

Phe Leu His Asp Val Ser Glu Gly Asn Asp Pro Ser Val Gly Lys Asn
                245                 250                 255

Val Lys Glu Leu Val Ala Tyr Ile Ser Thr Ser Gly Glu Lys Asp Ala
            260                 265                 270

Gly Thr Asp Asp Tyr Met Tyr Phe Gly Ile Lys Thr Lys Asp Gly Lys
        275                 280                 285

Thr Gln Glu Trp Glu Met Asp Asn Pro Gly Asn Asp Phe Met Thr Gly
    290                 295                 300

Ser Lys Asp Thr Tyr Thr Phe Lys Leu Lys Asp Glu Asn Leu Lys Ile
305                 310                 315                 320

Asp Asp Ile Gln Asn Met Trp Ile Arg Lys Arg Lys Tyr Thr Ala Phe
                325                 330                 335

Pro Asp Ala Tyr Lys Pro Glu Asn Ile Lys Val Ile Ala Asn Gly Lys
            340                 345                 350

Val Val Val Asp Lys Asp Ile Asn Glu Trp Ile Ser Gly Asn Ser Thr
        355                 360                 365

Tyr Asn Ile Lys
    370

<210> SEQ ID NO 13
<211> LENGTH: 4
<212> TYPE: PRT
<213> ORGANISM: Artificial sequence
<220> FEATURE:
<221> NAME/KEY: MISC_FEATURE
<222> LOCATION: (1)..(4)
<223> OTHER INFORMATION: Endoplasmic reticulum retention signal

<400> SEQUENCE: 13

Lys Asp Glu Leu
1

<210> SEQ ID NO 14
<211> LENGTH: 54
<212> TYPE: DNA
<213> ORGANISM: Artificial sequence
<220> FEATURE:
<223> OTHER INFORMATION: PCR amplification Primer with an SpeI
```

-continued

```
<400> SEQUENCE: 14
agagaactag taaaaaggag aaatccatgc atcaccatca ccatcactcc gcgg        54

<210> SEQ ID NO 15
<211> LENGTH: 40
<212> TYPE: DNA
<213> ORGANISM: Artificial sequence
<220> FEATURE:
<223> OTHER INFORMATION: PCR amplification Primer with a XhoI
      restriction site

<400> SEQUENCE: 15
agagactcga gctatcattt gatattgtag gttgaattgc                        40

<210> SEQ ID NO 16
<211> LENGTH: 58
<212> TYPE: DNA
<213> ORGANISM: Artificial sequence
<220> FEATURE:
<223> OTHER INFORMATION: PCR amplification Primer with a SpeI
      restriction site

<400> SEQUENCE: 16
agagaactag taaaaaggag aaatccatga gttgggatgg aaagattgat ggcactgg    58
```